United States Patent
Seco et al.

(10) Patent No.: US 11,331,519 B2
(45) Date of Patent: May 17, 2022

(54) DETECTOR AND METHOD FOR TRACKING AN ARRIVAL TIME OF SINGLE PARTICLES IN AN ION BEAM

(71) Applicants: Deutsches Krebsforschungszentrum, Heidelberg (DE); Universitat Politecnica de Valencia, Valencia (ES); Consejo Superior de Investigaciones Cientificas, Madrid (ES)

(72) Inventors: Joao Seco, Heidelberg (DE); Paulo Jorge Magalhaes Martins, Heidelberg (DE); Riccardo Dal Bello, Heidelberg (DE); Michael Seimetz, Valencia (ES)

(73) Assignees: Deutsches Krebsforschungszentrum, Heidelberg (DE); Universitat Politecnica de Valencia, Valencia (ES); Consejo Superior de Investigaciones Cientificas, Madrid (ES)

( * ) Notice: Subject to any disclaimer, the term of this patent is extended or adjusted under 35 U.S.C. 154(b) by 484 days.

(21) Appl. No.: 16/375,322

(22) Filed: Apr. 4, 2019

(65) Prior Publication Data
US 2020/0316404 A1 Oct. 8, 2020

(51) Int. Cl.
*A61N 5/10* (2006.01)
*G01T 1/20* (2006.01)
(Continued)

(52) U.S. Cl.
CPC .......... *A61N 5/1071* (2013.01); *A61B 6/4258* (2013.01); *G01T 1/201* (2013.01);
(Continued)

(58) Field of Classification Search
CPC .......... A61N 5/1071; A61N 2005/1087; A61N 5/1077; G01T 1/201; G01T 1/2006; G01T 1/203; G01T 1/29; A61B 6/4258
See application file for complete search history.

(56) References Cited

U.S. PATENT DOCUMENTS

| 4,942,302 A | 7/1990 | Koechner |
|---|---|---|
| 8,026,489 B2 | 9/2011 | Haguenauer et al. |

(Continued)

FOREIGN PATENT DOCUMENTS

| KR | 20100132835 A * | 12/2010 | |
|---|---|---|---|
| WO | WO 2015/040225 A1 | 3/2015 | |
| WO | WO-2020051257 A9 * | 7/2020 | ............... G01T 3/06 |

OTHER PUBLICATIONS

Krimmer et al., Prompt-Gamma Monitoring in Hadrontherapy: A Review, Nuclear Instruments and Methods in Physics Research, A, 2018, pp. 58-73.

(Continued)

*Primary Examiner* — Marcus H Taningco
(74) *Attorney, Agent, or Firm* — Bose McKinney & Evans LLP

(57) ABSTRACT

A detector and a method for tracking an arrival time of single particles in an ion beam are disclosed, wherein the single particles are provided as a bunch of ions by a synchrotron. Herein, the detector comprises a detector segment comprising a scintillating material, the scintillating material being designated for generating radiation upon passing of a single particle comprised by the bunch of ions through the scintillating material, wherein the scintillating material comprises a plurality of scintillating fibers, the scintillating fibers being provided as a fiber layer, wherein the fiber layer is located perpendicularly with respect to a direction of the incident ion beam; at least one detector element, the detector element being designated for generating a detector signal from the radiation; and at least one evaluation device, the evaluation device being designated for determining information about the single particles from the detector signals provided by the at least one detector element.

19 Claims, 7 Drawing Sheets

(51) Int. Cl.
    *A61B 6/00*    (2006.01)
    *G01T 1/203*   (2006.01)
(52) U.S. Cl.
    CPC .......... *G01T 1/203* (2013.01); *G01T 1/2006* (2013.01); *A61N 2005/1087* (2013.01)

(56) References Cited

U.S. PATENT DOCUMENTS

2011/0057110 A1   3/2011  Testa et al.
2018/0078790 A1*  3/2018  Lee ................... A61N 5/1077

OTHER PUBLICATIONS

Hueso-González et al., A Full-Scale Clinical Prototype for Proton Range Verification Using Prompt Gamma-Ray Spectroscopy, Physics in Medicine & Biology, 2018, pp. 1-20.

Xie et al., Prompt Gamma Imaging for In Vivo Range Verification of Pencil Beam Scanning Proton Therapy, Int'l J. Radiation Oncology, 2017, pp. 210-218.

Duk et al., Performance Studies of the Hodoscope Prototype for the NA62 Experiment, J. Instrumentation, 2016, 10 pages.

Neet, Beam Profile Monitors for Fast and Slow Extraction Proton Beams, Presented to Nat'l Accelerator Conference, 1969, 5 pages.

Braccini et al., A Beam Monitor Detector Based on Doped Silica and Optical Fibres, J. Instrumentation, 2012, 14 pages.

Laux et al., Beam Profile Measurements of Intense Heavy-Ion Beams, Proc. of 4th European Particle Accelerator Conference, 1994, pp. 1664-1666.

Leverington et al., A Prototype Scintillating Fibre Beam Profile Monitor for Ion Therapy Beams, J. Instrumentation, 2018, 19 pages.

Vignati et al., Innovative Strip Silicon Detectors for Proton Beam Monitoring: Preliminary Results, Int'l J. Particle Therapy, p. 79.

Graeff et al., Helium as a Range Probe in Carbon Ion Therapy, Abstracts/Physica Medica, 2018, p. 11.

Mazzucconi et al., Mixed Particle Beam for Simultaneous Treatment and Online Range Verification in Carbon Ion Therapy: Proof-of-Concept Study, Medical Physics, 2018, pp. 5234-5243.

P. Martins et al., Presentation Material entitled Towards prompt gamma spectroscopy for C-12 range control: development of a synchrotron-dedicated system, 57th Annual Meeting of the Particle Therapy Cooperative Group, May 25, 2018, 15 pages.

* cited by examiner

DETECTOR AND METHOD FOR TRACKING AN ARRIVAL TIME OF SINGLE PARTICLES IN AN ION BEAM

BACKGROUND

This disclosure relates to a detector and a method for tracking an arrival time of single particles in an ion beam, in particular for tracking single particles within in a bunch of ions as provided by a synchrotron. Further, this disclosure relates to a method for determining a type of single particles in the ion beam as well as to an apparatus and a method for verification of a particle range and a dose delivery in a tissue of a patient. The devices and the methods according to this disclosure may, preferably, be used in the field of ion beam therapy, specifically for a range control of ion beams being generated in a synchrotron and traveling through matter, especially towards a tumorous tissue of a patient. However, other kinds of applications are also possible.

Particle therapy with hadron beams, wherein the hadrons are ions which are specifically selected from protons or from ions of helium, carbon or oxygen, has a high clinical potential in terms of efficacy and effectiveness. Ion beams which comprise carbon ions are particularly promising since they exhibit reduced lateral spread and increased biological effect. It is generally important in particle therapy to prevent healthy organs of a patient from receiving radiation, in particular particles as provided by the ion beam. For this purpose, it is known to employ a so-called "Bragg peak" to significantly reduce side effects to the patient. As generally used, the term "Bragg peak" refers to a pronounced peak within a so-called "Bragg curve" which denotes a graphical representation of the energy loss of the incident ion beam with respect to a traveling distance of the ion beam through matter, specifically through the tissue of the patient. Ion beams exhibit the advantageous effect that the Bragg peak occurs immediately before the ions come to rest within the matter, in particular within the tissue of the patient. Thus, in order to solve the above-indicated problem of preventing healthy organs from receiving radiation, an improved range control with respect to a location of the Bragg peak within the tissue is desirable. Herein, it is particularly intended to apply a kind of range verification which is capable of reducing range uncertainties and, therefore, safety margins as far as possible.

Among the techniques which are used for a range verification of ion beams in the tissue of a patient, prompt-gamma imaging has been demonstrated in the clinical environment as the one with the most promising features for a real-time tracking of the ion beam. Conversely to other range verification techniques, such as positron emission tomography that relies on an emission of photons on a much longer time scale, prompt-gamma imaging allows, due to a nearly instantaneous emission of the gamma radiation resulting from a nuclear interaction of the ion beam with the tissue, a prompt detection of emitted gamma radiation. Whereas it has already been demonstrated that prompt-gamma imaging is suitable for proton range verification in a cyclotron, the range verification for ion beams which are generated in a synchrotron can still be improved. While for ion beams being generated in a cyclotron a good correlation exists between a radio frequency as used in this kind of accelerator and a temporal microstructure of the generated ion beam which can be used for indirect determination of time-of-flight (TOF) information, this kind of correlation completely fails for ion beams which are generated in a synchrotron. Due to different acceleration processes in a synchrotron compared to a cyclotron, an ion beam which is generated in a synchrotron exhibits an irregular microscopic time structure which destroys this kind of correlation. Consequently, this disclosure aims to determine TOF information between a primary ion beam which is generated in a synchrotron and the prompt-gamma signal as monitored by a gamma ray detector.

J. Krimmer, D. Dauvergne, J. M. Létang, and É. Testa, *Prompt-gamma monitoring in hadrontherapy: A review*, Nuclear Instruments and Methods in Physics Research Section A: Accelerators, Spectrometers, Detectors and Associated Equipment 878, 2018, pp. 58-73, present a review and discuss the state of the art for all techniques using prompt-gamma detection to improve the quality assurance in hadron therapy. Herein, secondary radiation emission induced by nuclear reactions is correlated to the path of ions in matter. Therefore, such penetrating radiation can be used for in vivo control of hadron therapy treatments, for which a primary beam is absorbed inside a patient. Among secondary radiations, prompt-gamma rays were proposed for real-time verification of ion range. Such verification is a desired condition to reduce uncertainties in treatment planning. This review covers efforts which have been undertaken worldwide for more than a decade in order to promote prompt-gamma based devices to be used in clinical conditions. Dedicated cameras are necessary to overcome the challenges of a broad- and high-energy distribution, a large background, high instantaneous count rates, and compatibility constraints with patient irradiation. Several types of prompt-gamma imaging devices have been proposed which are either physically-collimated or electronically collimated. In addition, other methods than direct prompt-gamma imaging were proposed, which are based on specific counting using either time-of-flight or photon energy measurements.

Fernando Hueso-González, Moritz Rabe, Thomas A Ruggieri, Thomas Bortfeld and Joost M Verburg, *A full-scale clinical prototype for proton range verification using prompt gamma-ray spectroscopy*, Phys. Med. Biol. 63, 2018, 185019, present a full-scale clinical prototype system for in vivo range verification of proton pencil-beams using the prompt gamma-ray spectroscopy method. The detection system consists of eight $LaBr_3$ scintillators and a tungsten collimator, mounted on a rotating frame. Custom electronics and calibration algorithms have been developed for measurement of energy- and time-resolved gamma-ray spectra during proton irradiation at a clinical dose rate. Using experimentally determined nuclear reaction cross-sections and a GPU-accelerated Monte Carlo simulation, a detailed model of the expected gamma-ray emissions is created for each individual pencil-beam. The absolute range of the proton pencil-beams is determined by minimizing the discrepancy between the measurement and this model, leaving the absolute range of the beam and the elemental concentrations of the irradiated matter as free parameters. The system was characterized in a clinical-like situation by irradiating different phantoms with a scanning pencil-beam. A dose of 0.9 Gy was delivered to a $5 \times 10 \times 10$ $cm^3$ target with a beam current of 2 nA incident on a phantom. Different range shifters and materials were used to test the robustness of the verification method and to calculate the accuracy of the detected range. The absolute proton range was determined for each spot of the distal energy layer with a mean statistical precision of 1.1 mm at a 95% confidence level and a mean systematic deviation of 0.5 mm, when aggregating pencil-beam spots within a cylindrical region of 10 mm radius and 10 mm depth. Small range errors deliberately introduced were successfully detected and even large differences in the elemental composition do not affect the range verification accuracy. As a result, this system is suitable for range verification during patient treatments in clinical studies. However, this system is designed for cyclotrons in which a well-correlated arrival time of the incident particles with the radio frequency of the cyclotron can be observed.

Yunhe Xie, El Hassane Bentefour, Guillaume Janssens, Julien Smeets, Francois Vander Stappen, Lucian Hotoiu, Lingshu Yin, Derek Dolney, Stephen Avery, Fionnbarr O'Grady, Damien Prieels, James McDonough, Timothy D. Solberg, Robert A. Lustig, Alexander Lin, and Boon-Keng K. Teo, *Prompt Gamma Imaging for In Vivo Range Verification of Pencil Beam Scanning Proton Therapy*, Radiation Oncology, Vol. 99 (2017), p. 210-218, report clinical results and value assessment of prompt-gamma imaging for in vivo proton range verification in a pencil-beam scanning mode which is, specifically, designed for a use in cyclotrons. A stand-alone, trolley-mounted, prototype prompt-gamma camera utilizing a knife-edge slit collimator design was used for recording the prompt-gamma signal as emitted along proton tracks during delivery of proton therapy for a brain cancer patient. The recorded prompt-gamma depth detection profiles of individual pencil-beam spots were compared with expected profiles simulated from a treatment plan.

U.S. Publication No. 2011/0057110 A1 discloses a method for real-time measurement of a local dose received by a region of a target upon bombardment of the target by an incident beam of hadrons which generates at least prompt-gamma rays and neutrons. The particles emitted by the target are measured by collimating the region of the target and by placing a detector at a distance from the region of the target to be measured. The detector is linked to a device for particle energy and time-of-flight measurement, such as to a hodoscope which comprises scintillating fibers or a polycrystalline diamond detector. The number of prompt-gamma rays received by the detector is determined by selecting the recorded events, and a two-directional charged-particle detection system, placed in the beam of incident hadrons before the target, is used so as to obtain the transverse position of the incident hadrons in order to provide spatial information of the beam.

WO 2015/040225 A1 discloses a device and a method for the monitoring of the range of a particle radiation of a cyclotron as radiation device for radiation therapy with at least one detector being able to detect single gamma particles and at least one analyzer. When detecting a gamma particle (event), a signal is created in the detector, whereby the signal is correlated in time with the arrival of the gamma particle in the detector. The analyzer analyzing the signal of the detector assigns a time of detection to either every event or to selected events. The radiation device or a separate particle detector provides a reference signal which is correlated to the emersion of single particles or particle bunches from the radiation device with an uncertainty in time of ≤10 ns. The technique which is also known as prompt-gamma timing (PGT) correlates a time difference between the arrival of the incident protons in the entrance plane of the target and the time of detection of the prompt gamma at the gamma detector. Prompt gamma from protons which travel further in the target are detected later than those stopping earlier, which results in time distribution shifts that can be correlated with the proton range.

Further, V. Duk, S. Kholodenko, S. Fedotov, M. Giorgi, E. Gushchin, A. Khudyakov, A. Kleymenova, Y. Kudenko, V. Kurshetsov, I. Mannelli, V. Obraztsov, A. Ostankov, V. Semenov, and V. Sugonyaev, *Performance studies of the hodoscope prototype for the NA62 experiment*, Journal of Instrumentation 11, 2016, No. 06, P06001, describe a hodoscope prototype designed for detecting charged particles which has been installed and exposed to a beam during a data taking period in the scope of experimental high-energy particle physics. Efficiency and time resolution for hodoscope tiles are measured. The average signal amplitude is estimated from the efficiency curves. The results of the tests have led to several improvements in the final design of the hodoscope.

U.S. Pat. No. 8,026,489 B2 discloses a device for characterizing a particle beam comprising at least one detector including a fiber-optic network coupled to an image sensor comprising a CCD or CMOS sensor. This device is used for spatial tracking of the incident beam.

U.S. Pat. No. 4,942,302 A discloses a large area nuclear detection system with two linear arrays of orthogonally-arranged optical fibers for detecting with high degree of accuracy and resolution the nuclear particles in accordance with the quantity of energy received from the fibers.

Neet, D. A. G., *Beam profile monitors for fast and slow extraction proton beams*, 1969, CERN-ISR-CO/69-4, CERN describes two beam profile monitors designed for the beam transfer system of the 29 GeV intersecting storage rings. The presented sensitivity is enough to measure single proton synchrotron bunches with a density of $2 \times 10^{10}$ protons/cm$^2$. Various inorganic materials were tested, such as zinc sulfide, cerium activated lithium glass, sapphire, and quartz.

S. Braccini, A. Ereditato, F. Giacoppo, I. Kreslo, K. P. Nesteruk, M. Nirkko, M. Weber, P. Scampoli, M. Neff, S. Pilz and V. Romano, *A beam monitor detector based on doped silica and optical fibres*, JINST 7, 2012, T02001, describe a detector prototype based on doped silica fibers coupled to optical fibers designed for accelerators used in medical applications. Tests were performed with a 2 MeV proton pulsed beam and an intensity of $5 \times 10^{12}$ protons/s.

Laux, W., Spiller, P., Dornik, M. and Hoffmann D. H. H, *Beam profile measurements of intense heavy-ion beams* describe a cerium-doped quartz glass detector with a linear scintillation efficiency up to $6 \times 10^9$ Ne-ions/mm$^2$, Fourth European Particle Accelerator Conference—EPAC 94, London, England. They show good spatial resolution, radiation hardness and the ability to discriminate bunches 250 ns apart.

B. D. Leverington, M. Dziewiecki, L. Renner and R. Runze, *A prototype scintillating fibre beam profile monitor for Ion Therapy beams*, JINST, 2018, 13, P05003, describe a beam profile monitor comprising plastic scintillating fibers to determine the beam property reconstruction performance at the HIT facility. This detector was designed for spatial tracking of the incident ion-beams and as a surrogate means of the currently used multi wire proportional chambers (MWPC). The detector was adapted from the one used at the experiment LHCb, CERN. However, the detector thickness is still not acceptable for clinical use. The radiation hardness is also a major concern raised by the authors. The integration time needed for an acceptable SNR also limits the readout rate of the beam position to values similar to the MWPCs. The readout rate is still limited to 1-3 kHz.

A Vignati, Z Ahmadi Ganjeh, A Attili, M Boscardin, N Cartiglia, G F Dalla Betta, M Donetti, F Fausti, M Ferrero, F Ficorella, S Giordanengo, O Hammad Ali, M Mandurrino, L Manganaro, G Mazza, V Monaco, L. Pancheri, G Paternoster, R Sacchi, Z Shakarami, V Sola, A Staiano, R Cirio, *Innovative strip silicon detectors for proton beam monitoring: preliminary results*, 2018, PTCOG57, Cincinnati, USA, describe a competitive detector based on solid state detectors capable of tracking the time information of single particles for radiobiological applications with a time resolution of tens of ps. They were able to count individual protons in 3×3 cm$^2$ for an intensity of 10$^8$ protons/s cm$^2$. The major disadvantages are the readout complexity and the radiation hardness of those detectors.

Christian Graeff, Uli Weber, Christoph Schuy, Nami Saito, Lennart Volz, Pierluigi Piersimoni, Joao Seco, Michael Kraemer, *Helium as a range probe in carbon ion therapy*, Physica Medica, 2018, OA027, investigate the feasibility of simultaneously treating the patient with Carbon ions and detecting Helium exiting the patient to access the beam range. This is accomplished by mixing beams with 90% Carbon and 10% Helium. The methods within this disclosure for determining a type of single particles in an ion beam could be applied for diagnosing such mixed beams.

Davide Mazzucconi, Stefano Agosteo, Michele Ferrarini, Luigi Fontana, Valeria Lante, Marco Pullia, and Simone Savazzi, Mixed particle beam for simultaneous treatment and online range verification in carbon ion therapy: Proof-of-concept study, 2018, Medical Physics, 45 (11), describe a similar method for both treating and imaging a patient with mixed beams of Carbon and Helium. The imaging system comprises a plastic scintillator observed by a CCD camera.

SUMMARY

This disclosure teaches a detector and a method for tracking an arrival time of single particles in an ion beam, a method for determining a type of single particles in an ion beam as well as an apparatus and a method for verification of a particle range and a dose delivery in a tissue of a patient, which at least partially avoid the disadvantages of known detectors and methods.

In particular, this disclosure teaches a detector and a method which enable single particle tracking inside a bunch of ions as provided by a synchrotron, wherein the ion beam exhibits clinical intensities. Specifically, a time resolution of a nanosecond or below is obtained and a minimal interaction of the detector with the ion beam before the ion beam reaches the tissue of a patient is achieved, wherein the detector is capable of covering a scanning area of approximately 20×20 cm$^2$ within the tissue of the patient.

This disclosure teaches a detector and a method for time tracking of particles, in particular of single particles, in an ion beam, a method for determining a type of single particles in an ion beam as well as an apparatus and a method for verification of a particle range and a dose delivery in a tissue of a patient. Embodiments incorporating this disclosure may be realized in an isolated way or in any arbitrary combination.

As used in the present specification, the term "comprising" or grammatical variations thereof, are to be taken to specify the presence of stated features, integers, steps or components or groups thereof, but do not preclude the presence or addition of one or more other features, integers, steps, components or groups thereof. The same applies to the term "having" or grammatical variations thereof, which is used as a synonym for the term "comprising." Both "comprising" and "having" are to be interpreted as "open-ended," as understood in U.S. patent practice.

It shall be understood that various terms used throughout this disclosure and claims should not receive a singular interpretation unless it is made explicit herein. By way of non-limiting example, the terms "detector element," "evaluation device" and "readout bundle," to name just a few, should be interpreted when appearing in this disclosure and claims to mean one or more. All other terms used herein should be similarly interpreted unless it is made explicit that a singular interpretation is intended.

In a first aspect of this disclosure, a detector for tracking an arrival time of single particles in an ion beam is disclosed, wherein the single particles are provided as a bunch of ions by a synchrotron, wherein the detector comprises:

a detector segment comprising a scintillating material, the scintillating material being designated for generating radiation upon passing of a single particle comprised by the bunch of ions through the scintillating material, wherein the scintillating material comprises a plurality of scintillating fibers, the scintillating fibers being provided as a fiber layer, wherein the fiber layer is located perpendicularly with respect to a direction of the incident ion beam;

at least one detector element, the detector element being designated for generating a detector signal from the radiation; and at least one evaluation device, the evaluation device being designated for determining tracking information about the single particles from the detector signals provided by the at least one detector element.

Accordingly, the detector for tracking the arrival time of the single particles in the ion beam may, preferably, be used for particle therapy of a tumorous tissue of a patient. Herein, the tumorous tissue may comprise a tumorous modification which may have been introduced into the tissue of the patient by cancer. As generally used, the term "cancer" refers to a disease of an animal, in particular of a mammal and, especially, of a human, which is characterized by an uncontrolled growth by a group of body cells, usually denoted as "cancer cells." This uncontrolled growth may be accompanied by intrusion into and destruction of surrounding tissue (i.e., "invasion") and possibly spread of cancer cells to other locations in the body (i.e., "metastasis"). Preferably, the cancer may be selected from the list consisting of: acute lymphoblastic leukemia, acute myeloid leukemia, adrenocortical carcinoma, aids-related lymphoma, anal cancer, appendix cancer, astrocytoma, atypical teratoid, basal cell carcinoma, bile duct cancer, bladder cancer, brain stem glioma, breast cancer, burkitt lymphoma, carcinoid tumor, cerebellar astrocytoma, cervical cancer, chordoma, chronic lymphocytic leukemia, chronic myelogenous leukemia, colon cancer, colorectal cancer, craniopharyngioma, endometrial cancer, ependymoblastoma, ependymoma, esophageal cancer, extracranial germ cell tumor, extragonadal germ cell tumor, extrahepatic bile duct cancer, gallbladder cancer, gastric cancer, gastrointestinal stromal tumor, gestational trophoblastic tumor, hairy cell leukemia, head and neck cancer, hepatocellular cancer, hodgkin lymphoma, hypopharyngeal cancer, hypothalamic and visual pathway glioma, intraocular melanoma, kaposi sarcoma, laryngeal cancer, medulloblastoma, medulloepithelioma, melanoma, merkel cell carcinoma, mesothelioma, mouth cancer, multiple endocrine neoplasia syndrome, multiple myeloma, mycosis fungoides, nasal cavity and paranasal sinus cancer, nasopharyngeal cancer, neuroblastoma, non-hodgkin lymphoma, non-small cell lung cancer, oral cancer, oropharyngeal cancer, osteosarcoma, ovarian cancer, ovarian epithelial cancer, ovarian germ cell tumor, ovarian low malignant potential tumor, pancreatic cancer, papillomatosis, paranasal sinus and nasal cavity cancer, parathyroid cancer, penile cancer, pharynx-geal cancer, pheochromocytoma, pituitary tumor, pleuropulmonary blastoma, primary central nervous system lymphoma, prostate cancer, rectal cancer, renal cell cancer, retinoblastoma, rhabdomyosarcoma, salivary gland cancer, sézary syndrome, small cell lung cancer, small intestine cancer, soft tissue sarcoma, squamous cell carcinoma, squamous neck cancer, testicular cancer, throat cancer, thymic carcinoma, thymoma, thyroid cancer, urethral cancer, uterine sarcoma, vaginal cancer, vulvar cancer, waldenström macroglobulinemia, and wilms tumor.

As generally used, the incident ion beam, also denoted as "hadron beam," may comprise ions or hadrons which propagate along a direction of the ion beam. Specifically, the ions or hadrons which are, preferably, used in the context of this disclosure are selected from protons $^1p$ or from ions of helium $^4He$, of carbon $^{12}C$ or of oxygen $^{16}O$, in particular, since each of these kinds of ions, which may also be denoted by the term "type" of ions, has a high clinical potential in terms of efficacy and effectiveness. Herein, carbon ions $^{12}C$ are, especially, preferred since they exhibit reduced lateral spread and increased biological effect.

Herein, the ion beams which are used for this disclosure are provided by a synchrotron. As generally used, a "synchrotron" refers to a cyclic particle accelerator, in which particles are accelerated by using a combination of electric fields and magnetic fields in order to travel around a fixed closed-loop path. Compared to a cyclotron, in which the particles travel in a spiral since the applied magnetic field is constant, the magnetic field in the synchrotron is continuously adjusted in a manner which allows keeping the accelerated particles in a circular orbit within a so-called "storage ring." A portion of the particles that are provided in this fashion are, then, used for generating the desired ion beams which travel in one or more beamlines. As demonstrated below in more detail, the ion beam which is formed in this fashion, moreover, comprises bunches of ions in which, generally, a plurality of single particles travel together.

Thus, as already indicated above, while a good correlation between a radio frequency and a temporal microstructure of the ion beam exists for ion beams generated in cyclotron-based facilities, such a correlation completely fails for ion beams which are generated in synchrotron-based facilities, specifically due to a different kind of beam extraction from the synchrotron. Thus, the ion beams which are generated in a synchrotron exhibit an irregular microscopic time structure which is not well-correlated with the radio frequency of the synchrotron. As a result, the radio frequency as used for accelerating the particles in the synchrotron cannot be used for indirectly determining time-of-flight (TOF) information concerning the generated ion beam, preferably having clinical intensities, in synchrotron-based facilities. Herein, intensities which are considered as "clinically applicable," however, depend on the hadrons used for the ion beam. Specifically, while clinical intensities for protons typically are $8\times10^7$ p/s to $3.2\times10^9$ p/s, clinical intensities for carbon ions are lower, preferably $2\times10^6$ p/s to $8\times10^7$ $^{12}C$/s. In general, other ranges are applicable for different kinds of ions.

In order to nevertheless be capable of single particle tracking at clinical intensities, the present detector for tracking the arrival time of the single particles in the ion beam comprises a detector segment, at least one detector element and an evaluation device as described herein. As generally used, the term "detector" refers to a device which is designated for determining at least whether a particular species, here a single particle being provided by an incident ion beam, is present or absent at a location of the detector.

As already indicated above, the detector for tracking the arrival time of the single particles in the ion beam according to this disclosure comprises at least one detector segment. As generally used, the term "detector segment" refers to a part of the detector which is able to receive the species to be detected, wherein a reaction between the species and the detector segment is capable of providing a measureable signal by the detector segment. With particular respect to this disclosure, the detector segment comprises a scintillating material, wherein the scintillating material is designated for generating radiation upon passing of an ionic particle as comprised by the bunch of ions through the scintillating material. As generally used, the "scintillating material" is or comprises a substance which, upon excitement by an incident ionic particle, absorbs a portion of the energy of the incident ionic particle and re-emits a further portion thereof in form of radiation, specifically within the ultraviolet, visual, and/or infrared spectral range, wherein this kind of radiation is also denoted by the term "scintillation." Herein, an incident of exciting the scintillating material by an ionic particle, which results in a subsequent observation of radiation generated by this incident, is, generally, denominated by the term "event."

In accordance with this disclosure, the scintillating material comprises a plurality of scintillating fibers. As generally used, the term "fiber" refers to a body being extended in a single direction, thus, exceeding the dimensions in the other directions by a factor of at least 10, preferably of at least 20, more preferred of at least 50. Herein, the scintillating fibers as typically used comprise a core of a first polymer material, such as a polystyrene-based polymer, wherein fluorescent dopants which are selected for producing the desired scintillation are incorporated by the first polymer material. Further, the core is typically clad by a cladding of a second polymer material, such as poly (methyl methacrylate) (PMMA) selected for proving high internal reflection in order to increase a signal-to-noise ratio. However, other kinds of scintillating fibers or materials thereof are also feasible. The scintillating fibers assume a cross-section which, typically, has a square or a round form and may, preferably, exhibit a size of 10 μm to 10 mm, wherein a cross-section of 100 μm to 2 mm may be preferred and wherein a cross-section of 250 μm to 1 mm may be more preferred.

A plurality of the scintillating fibers may be provided as a fiber layer. Herein, the fiber layer may, preferably, comprise 10 to 20,000 individual scintillating fibers, more preferred of 60 to 800 individual scintillating fibers. The plurality of the scintillating fibers can be located in a side-by-side arranged in form of a ribbon, thereby generating a so-called "fiber layer." Herein, the fiber layer may assume a polygon shape, preferably a rectangular or a square form of at least $5\times5$ mm$^2$, preferred of at least $1\times1$ cm$^2$, more preferred of at least $5\times5$ cm$^2$, most preferred of at least $10\times10$ cm$^2$, particularly preferred of at least $20\times20$ cm$^2$, thus providing a large scanning area.

Further, the fiber layer is located in a perpendicular manner with respect to a direction of the incident ion beam. As a result, the scintillating fibers as comprised by the fiber layer are also located perpendicularly with respect to the direction of the incident ion beam. As generally used, the term "direction" refers to a line of propagation of the incident ion beam impinging on the fiber layer. As generally used, the term "perpendicular" comprises an angle of 90°±45°, preferably of 90°±5°, preferably of 90°±1°, with respect to the direction of the incident ion beam. Similarly, the term "parallel" comprises an angle of 0°±45°, preferably of 0°±5°, preferably of 0°±1°, with respect to the direction of the incident ion beam. As a consequence of the perpendicular arrangement, the traversed material is minimized with minimal influence onto the properties of the ion beam.

As a result thereof, each ionic particle which impinges on one of the scintillating fibers within the fiber layer generates radiation, which can, subsequently, be detected by the at least one detector element. As generally used, the term "detector element" refers to an apparatus which is designated for generating a measurable detector signal from the incident radiation. Herein, the measurable detector signal may, preferably, be selected from an electrical signal, specifically an electrical voltage or an electrical current. In particular, the detector element may be selected from at least one of: a photomultiplier tube (PMT), a solid-state single-photon-sensitive device (silicon photomultiplier; SiPM), a charge-coupled device (CCD), a complementary metal-oxide-semiconductor (CMOS), or a quanta image sensor (QIS) chip. However, a further kind of detector element may also be feasible.

Such a kind of arrangement of a scintillating material may also be denominated by the term "time-of-flight (TOF) detector," wherein the TOF detector comprises a plurality of individual segments, each segment providing an amount of radiation upon impingement of an incident ionic particle, wherein the radiation is used for determination of information related to the incident ionic particle. However, other kind of detectors which are known as "hodoscopes" are arranged in a different manner in order to determine a spatial distribution of the incident ion bunch within a plane perpendicular to the direction of the incident ion beam but not the arrival time of the single particles.

In particular, for a purpose of obtaining a time resolution of a nanosecond or below ($\leq 1$ ns) between two consecutive events as defined above, the detector according to this disclosure comprises at least one individual detector element, wherein the detector element is designated for generating a detector signal from the incident radiation which impinges on the corresponding detector segment. In a first preferred embodiment, the detector according to this disclosure may, therefore, comprise exactly one individual detector segment which may be connected to an individual detector element by a single readout bundle, thus, contributing to a simple setup of the detector.

In a further preferred embodiment of this disclosure, the detector for tracking the arrival time of the single particles in the ion beam may comprise at least two detector elements, wherein each of the at least two detector elements may be connected to the scintillating fibers within the fiber layer in an alternating fashion. By way of example, two scintillating fibers which are located in an adjacent manner within the fiber layer are connected to two different detector elements, thus, forming two individual readout bundles which are independent with respect to each other. This feature may be implemented in a fashion that one or both sides of each scintillating fiber may slightly be removed from the fiber layer for being used as a fixed but detachable connection to the respective detector element. Herein, a double-side connection may allow for improved particle identification, increased background suppression. However, other kinds of connections between the scintillating fibers comprised by the fiber layer to the at least two detector elements may also be feasible.

As further already indicated above, the detector for tracking the arrival time of the single particles in the ion beam according to this disclosure further comprises at least one evaluation device. As generally used, the term "evaluation device" refers to an apparatus which is designated for determining information which is based on the detector signals that are provided by the at least one detector element to the evaluation device. For this purpose, a wire-based connection, or, alternatively or in addition, a wireless connection between the at least one detector element and the evaluation device may be provided. The evaluation device according to this disclosure is particularly designated for determining tracking information about the single particles, wherein the tracking information is based on the detector signals that are provided to the evaluation device by the at least one detector element.

In particular for a purpose of obtaining a time resolution of a nanosecond or below ($\leq 1$ ns) between two consecutive events as defined above, the evaluation device may comprise a fast analog-to-digital converter, preferably having a sampling rate of 10 ns, more preferably of 4 ns, more preferably of 1 ns or below. Herein, the fast analog-to-digital converter may, preferably, be selected from at least one of: a flash analog-to-digital converter (FADC), a field-programmable gate array (FPGA), a versa module eurocard (VME) digitizer, a time readout board (TRB), or an oscilloscope.

However, the detector segment of the detector according to this disclosure, on one hand, only absorbs a small portion of the energy of the incident ion beam, from which portion of energy the radiation is generated upon passing of a single particle as comprised by the bunch of ions through the detector segment. On the other hand, a further portion of the energy of the ion beam passes through the detector segment without being absorbed by the scintillating fibers which are comprised by the fiber layer which is located perpendicularly with respect to the direction of the incident ion beam. Rather, the further portion of the energy of the ion beam is designated for a treatment of a tumorous tissue of a patient as described above. As described below in more detail, the further portion of the energy of the ion beam can now be delivered towards the tissue of the patient which is designated for receiving the desired radiation for treatment of the corresponding cancer. As a result thereof, the ion beam may impinge on the tissue of the patient in a fashion that the incident ion beam may generate there at least prompt-gamma radiation, neutrons, β-emitters and secondary charged particles. As for example described in U.S. Publication No. 2011/0057110 A1, which is hereby incorporated herein by reference, the further detector may be placed at a distance from the tissue, wherein the further detector may be a device for particle energy and time-of-flight measurement in which prompt-gamma radiation may be received and determined. However, other kinds of measuring prompt-gamma radiation may also be feasible.

In a further aspect of this disclosure, a method for tracking an arrival time of single particles in an ion beam is disclosed. Herein, the method according to this disclosure comprises at least the following steps, wherein, however, additional steps may further be performed. In one embodiment, the indicated steps may be performed in a sequential approach, wherein, however, a subsequent step may at least partially be performed concurrently with a previous step. In an alternative embodiment, the mentioned steps may be performed in an integrative approach or in a mixed approach combining the sequential approach and the integrative approach, in particular, for minimizing time and/or storing space required for performing the present method. In addition, further steps which are not indicated here may also be performed.

In particular, the method for tracking the arrival time of the single particles in an ion beam comprises the steps of:
delivering an incident ion beam being provided by a synchrotron to a fiber layer, the ion beam comprising single particles in a bunch of ions;

arranging the fiber layer in a manner that the incident ion beam impinges on the fiber layer perpendicularly with respect to a direction of the incident ion beam, wherein the fiber layer comprises a plurality of scintillating fibers, each of the scintillating fibers comprising a scintillating material, the scintillating material being designated for generating radiation upon passing of a single particle through the scintillating material;

generating a detector signal from the radiation in at least one detector element; and determining information about the single particles from the detector signals provided by the at least one detector element by using at least one evaluation device.

Accordingly, an incident ion beam which is provided by using by a synchrotron, wherein the ion beam comprises single particles in a bunch of ions, is delivered to a fiber layer, in specifically to a fiber layer as described above or below in more detail. Herein, the single particle is, preferably, selected from a proton or an ion of helium, carbon or oxygen. According to this disclosure, the fiber layer is arranged in a manner that the incident ion beam impinges on the fiber layer perpendicularly with respect to a direction of the incident ion beam, wherein the fiber layer comprises a plurality of scintillating fibers, wherein each of the scintillating fibers comprises a scintillating material, wherein the scintillating material is designated for generating radiation upon passing of a single particle through the scintillating material. Accordingly, a detector signal is generated from the radiation in the at least one detector element, wherein, in a particular embodiment, at least two detector elements may be alternatingly connected to the scintillating fibers within the fiber layer. Further, information about the single particles is determined from the detector signals provided by the at least one detector element by using the at least one evaluation device.

In a particularly preferred embodiment, the method according to this disclosure may further comprise a further step of delivering a portion of an energy of the incident ion beam, which passes unabsorbed through the detector segment, further to impinge on a tissue of a patient.

In a further particularly preferred embodiment, the method according to this disclosure may, additionally, comprise an additional step of measuring prompt-gamma radiation as generated by the portion of the energy of the ion beam which impinges on the tissue of the patient.

In a further aspect, this disclosure refers to a method for determining a type of single particles in an ion beam, wherein the method comprising the following steps of:

providing information about single particles by applying the method for tracking an arrival time of single particles in an ion beam as described elsewhere herein; and determining the type of the single particles in the ion beam by observing a course of an energy deposition on a fiber layer being connected to an individual detector element as described above or below in more detail.

As used in connection with this disclosure, the term "type" may refer to a particular species of ions being carried by the ion beam. As already indicated above, the type of the single particles may be selected from protons or ions of helium, carbon or oxygen or secondary fragments, mainly protons. In a particularly preferred embodiment, the type of the single particles in the ion beam may be determined by separating a contribution of at least one ion component, such as a contamination of protons within an ion beam of helium, carbon or oxygen ions, from an envelope curve which is provided by the course of the energy deposition on the fiber layer. For further details, reference may be made to the detailed description below provided for FIG. 5.

In a further aspect, this disclosure refers to an apparatus for verification of a particle range and a dose delivery in a tissue of a patient, wherein the apparatus comprises:

the detector for tracking an arrival time of single particles in an ion beam as described elsewhere herein, the ion beam passing through the detector while being delivered to the tissue of the patient;

a further detector being designated for determining prompt-gamma radiation generated by the interaction of the beam with the tissue of the patient; and a further evaluation device, the further evaluation device being designated for verification of the particle range and the dose delivery in the tissue of the patient.

As generally used, the term "verification" with respect to the particle range in the tissue of the patient and the dose delivery into the tissue of the patient refers to determining a location of the so-called "Bragg peak" within the tissue of the patient. As already indicated above, the term "Bragg peak" refers to a pronounced peak within a so-denominated "Bragg curve" which denotes a graphical representation of the energy loss of the incident ion beam with regard to a traveling distance of the ion beam through the tissue of the patient. Advantageously, the Bragg peak occurs immediately before the ions as provided by the ion beam come to rest within the tissue of the patient. Thus, in order to prevent healthy organs from receiving radiation to significantly reduce side effects to the patient, an online range verification which is capable of reducing range uncertainties and safety margins as far as possible during treatment of the tissue of the patient corresponds to an online verification of the particle range and the dose delivery in the tissue of the patient.

In a particularly preferred embodiment, the detector for tracking the arrival time of the single particles in the ion beam is placed perpendicular to the ion beam which is traveling from the synchrotron to the tissue of the patient. The perpendicular arrangement of the detector minimizes the traversed fiber material. The further detector for determining prompt-gamma radiation as being generated by the tissue of the patient may, preferably, be arranged in a perpendicular manner with respect to the direction of the incident ion beam. However, other kinds of arrangements may also be feasible.

In a further preferred embodiment, the further evaluation device as comprised by the further detector for determining prompt-gamma radiation and the evaluation device as comprised by the detector for tracking the arrival time of the single particles in the ion beam as already described above may, preferably, be integrated into a combined evaluation device. As a result thereof, both kinds of evaluation procedures can be run on the same internal processors, thus resulting in a saving of equipment. Further arrangements may comprise a single data acquisition board with multiple channels and a shared clock, multiple data acquisition boards with a synchronized shared clock, the inclusion of the digital signal processing into the FPGA to reduce the data stream and processing time.

In a further aspect, this disclosure refers to a method for verification of a particle range and a dose delivery in a tissue of a patient, wherein the method comprises the following steps of:

providing an apparatus for verification of a particle range and a dose delivery in a tissue of a patient as described elsewhere herein;

delivering an incident ion beam being provided by a synchrotron to the at least one detector segment, the ion beam comprising single particles in a bunch of ions;

tracking the arrival time of the single particles in the ion beam by applying the detector as described above or below in more detail;

delivering a portion of an energy of the ion beam which is not absorbed by the detector segment to the tissue of the patient, where the portion of an energy of the ion beam generates prompt-gamma radiation;

determining information about the prompt-gamma radiation being generated by an interaction of the beam with the tissue of the patient; and verifying the particle range and the dose delivery to the tissue of the patient based on the information about the prompt-gamma radiation.

For further details with respect to the method for tracking the arrival time of the single particles in the ion beam, to the method for determining a type of single particles in an ion beam as well as to the apparatus and method for the verification of the particle range and the dose delivery in a tissue of a patient, reference may be made to the detector according to this disclosure as described elsewhere in this document.

The devices and the methods according to this disclosure provide considerable advantages over known devices and methods. In particular, the detector and the method for tracking an arrival time of single particles in an ion beam according to this disclosure is capable of single particle tracking inside a bunch of ions as provided by a synchrotron, wherein the ion beam may exhibit clinical intensities. Herein, the time of arrival of the primary particles as determined hereby can be used in prompt-gamma applications and, moreover, in ion imaging applications. Specifically, it is possible to obtain a time resolution of a nanosecond or below and to achieve a minimal interaction of the detector with the ion beam before the ion beam reaches the tissue of a patient. Further, the detector is capable of covering of approximately 20×20 cm$^2$ as a scanning area within the tissue of the patient. In addition thereto, the devices and the methods according to this disclosure may allow determining detailed information about micro time structures and/or macro time structures of the incident ion beam, thus, being applicable for time-of-flight measurements. Further, particle identification based on energy deposition may also be possible for beam diagnostics of the incident ion beam.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein:

FIG. 5A) and a second photo multiplier tube (PMT2; FIG. 5B), respectively;

DESCRIPTION

Figure 1:
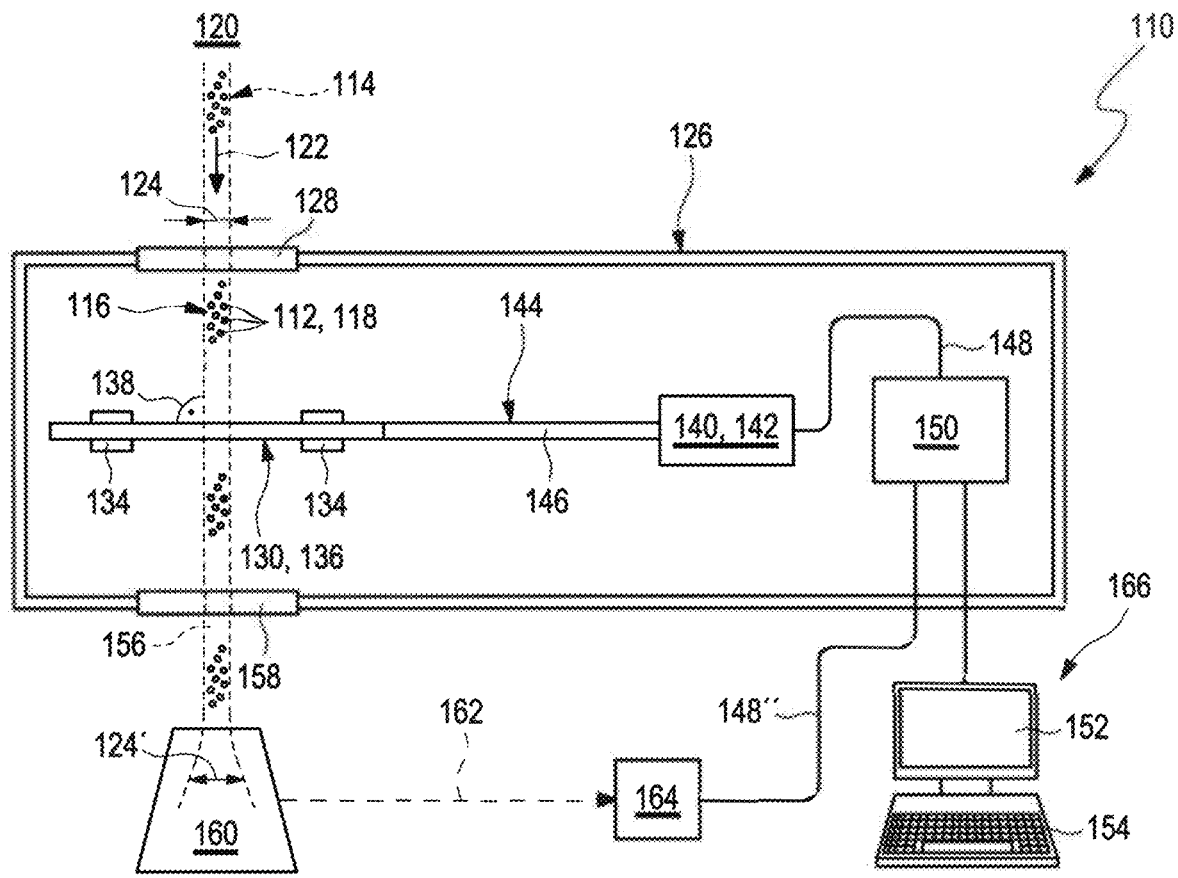
FIGS. 1A and 1B illustrate a preferred embodiment of a detector for tracking an arrival time of single particles in an ion beam and of an apparatus for verification of a particle range and a dose delivery in a tissue of a patient in accordance with the present invention in a top view (FIG. 1A) and a portion of the detector in a side view (FIG. 1B)
Figure 1:
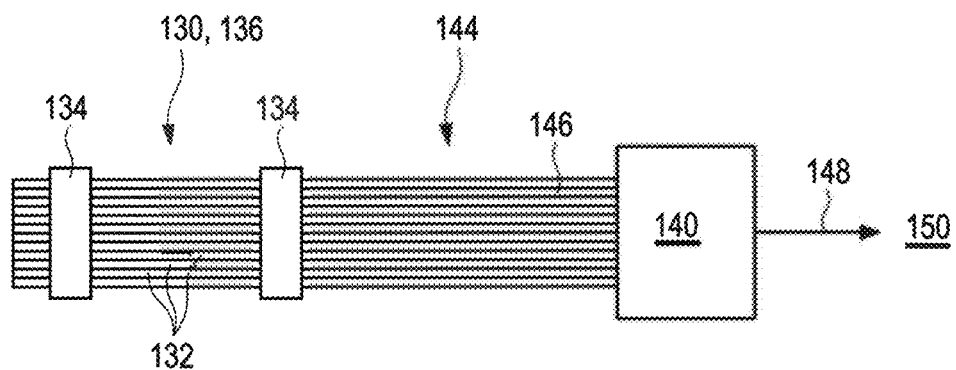

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

FIG. 1A illustrates, in a top view, a preferred embodiment of a detector 110 for tracking single particles 112 in an ion beam 114 in a top view according to this disclosure, wherein the single particles 112 are provided as a bunch 116 of hadrons or ions 118 by a synchrotron 120 and propagate along a direction 122 of the ion beam 114. As indicated above, the ions 118 which are, preferably, used in the context of this disclosure are selected from protons $^1$p or from ions of helium $^4$He, of carbon $^{12}$C or of oxygen $^{16}$O, specifically, since each of these kinds of ions 118 has a high clinical potential in terms of efficacy and effectiveness. Herein, carbon ions $^{12}$C are, especially, preferred since they exhibit a reduced lateral spread 124 both in the delivery step 224 and within the tissue 160 and allow an increased biological effect in the tissue of a patient to be treated by the single particles 112.

As further illustrated in FIG. 1A, the detector 110 may be comprised by a housing 126 which may be designated, in a first respect, for providing mechanical stability to the detector 110 and, in a further respect, for shielding the detector 110 or one or more partitions thereof from other kind of radiation, in particular visible light, apart from the ion beam 114. However, in order to allow the incident ion beam 114 entering the housing 126, an entrance window 128 may be provided within a portion of the housing 126, wherein the entrance window 128 may, especially, be designed for exhibiting a high transparency for those kinds of ions 118 which are comprised for the ion beam 114, such as $^{12}$C ions, and a low transparency for all other kind of radiation, in particular visible light. By way of example, a polymer sheet with or without a metallic layer, or at least one thin metal foil, specifically several layers of aluminized mylar or double aluminized mylar, may be used for this purpose.

The detector 110 comprises a detector segment 130 which is designated for receiving the incident ion beam 114 as well as for generating radiation upon passing of a single particle 112 as comprised by the bunch 116 of ions 118 through the detector segment 130. For this purpose, the detector segment 130 comprises a scintillating material 132 as schematically depicted in FIG. 1A, wherein the scintillating material 132 is designated for generating the desired signal upon an event, which is defined by a passing of the single particle 112 through the scintillating material 132. Herein, the scintillating material 132 may be or comprise a particular substance which, upon excitement by the incident ionic single particle 112, absorbs a portion of the energy of the incident ionic single particle 112 and re-emits a further portion of the energy of the incident ionic single particle 112 in form of radiation, which is, usually, denoted by the term "scintillation." In general, the scintillation comprises radiation within the ultraviolet, visual, and/or infrared spectral range.

According to this disclosure, the scintillating material 132 comprises a plurality of scintillating fibers 132 which, as illustrated in FIG. 1A, can be maintained in position by a specifically adapted mounting 134. The scintillating fibers 132 as typically used comprise a core of a first polymer material, such as a polystyrene-based polymer, wherein fluorescent dopants which are selected for producing the desired scintillation are incorporated by the first polymer material. Further, the core of the scintillating fibers 132 is typically clad by a cladding of a second polymer material, such as poly (methyl methacrylate) (PMMA) selected for proving high internal reflection in order to guide the scintillation light with a high signal-to-noise ratio towards the ends of the scintillating fibers 132 and, thus to the at least one detector element as described below in more detail. However, other kinds of scintillating fibers 132 or materials used for the scintillating fibers 132 are also feasible. The scintillating fibers 132 assume a cross-section which, typically, has a square or a round form and may, preferably, exhibit a size of 10 µm to 10 mm, wherein a cross-section of 100 µm to 2 mm may be preferred and wherein a cross-section of 250 µm to 1 mm may be more preferred for this disclosure.

Further according to this disclosure, the scintillating fibers 132 are provided as a fiber layer 136, wherein the fiber layer 136 is located in a perpendicular arrangement 138 with respect to the direction 122 of the incident ion beam 114. As a result, the scintillating fibers 132 which are comprised by the fiber layer 136 are also located in the perpendicular arrangement 138 with respect to the direction 122 of the incident ion beam 114. As defined above, the perpendicular arrangement 138 comprises an angle of 90°±45°, preferably of 90°±5°, preferably of 90°±1°, with respect to the direction 122 of the incident ion beam 114. As a consequence of the perpendicular arrangement 138 of the fiber layer 136 with respect to the direction 122 of the incident ion beam 114, the material traversed by the incident ion beam is minimized with minimal influence on the ion beam properties. Herein, the fiber layer 136 may, preferably, comprise 10 to 20,000 individual scintillating fibers 132, more preferred of 60 to 800 individual scintillating fibers 132. Hereby, the plurality of the scintillating fibers 132 is located in a side-by-side arrangement in form of a ribbon, thereby generating the fiber layer 136. Herein, the fiber layer 136 may assume a polygon shape, preferably a rectangular or a square form of at least 5×5 mm$^2$, preferred of at least 1×1 cm$^2$, more preferred of at least 5×5 cm$^2$, most preferred of at least 10×10 cm$^2$, particularly preferred of at least 20×20 cm$^2$, thus providing a large scanning area. However, other forms and areas for the fiber layer 136 may also be feasible.

In the embodiment as illustrated in FIG. 1A, the detector 110 comprises a single detector element 140 which is designated for generating a measurable detector signal from the scintillation. Herein, the detector signal may, preferably, be selected from an electrical signal, specifically an electrical voltage or an electrical current. However, other kinds of detector signals, such as an optical signal, can also be used here as an alternative or in addition. In a preferred embodiment, the detector element 140 may be a photomultiplier tube (PMT) 142, wherein, however, other kinds of detector elements 140, such as a solid-state single-photon-sensitive device (silicon photomultiplier; SiPM) or a charged coupled device (CCD) or a complementary metal oxide semiconductor (CMOS) or a quanta image sensor chip (QIS), may also be feasible. One of skill in the art would recognize other alternatives.

According to this disclosure, the detector element 140 is arranged in a fashion that it has a connection 144 to the scintillating fibers 132 as provided in the fiber layer 136. Herein, this kind of connection 144 may comprise a readout bundle 146 of each of the scintillating fibers 132 to the detector element 140. However, other kinds of connections 144 may also be feasible, specifically, an arrangement in which a readout bundle 146 may be present at each side of the scintillating fibers 132 to the detector element 140. This kind of arrangement which may allow a double-side readout may result in improved particle identification and an increased background suppression.

The detector signals which are provided by the detector element 140 are further delivered by a corresponding lead 148 to an evaluation device 150, wherein the evaluation device 150 (e.g., a processor or computer) is designated for determining information about the single particles 112 from the detector signals as provided by the detector element 140. For this purpose, a wire-based connection or, alternatively or in addition, a wireless connection, such as by using optical or radio frequency transmission, between the detector element 140 and the evaluation device 150 may be provided. In general, the evaluation device 150 may be inside or outside the housing 126. Preferably, the evaluation device 150 may be an independent device and connected to the detector 110 by the leads 148. In particular, the evaluation device 150 is designed for determining tracking information about the single particles 112, wherein the tracking information is based on the detector signals which are provided to the evaluation device 150 by the detector element 140.

As demonstrated below in more detail, a particular purpose of this disclosure is obtaining a time resolution of a nanosecond or below between the time of arrival of the single particles 112 measured by the detector 110 and the time of arrival of the prompt gamma radiation 162 measured by further detector 164. In order to achieve this time resolution, the evaluation device may, preferably, comprise a fast analog-to-digital converter which, in particular, has a sampling rate preferably of <10 ns, more preferably of <4 ns, more preferably of ≤1 ns. Specifically, the fast analog-to-digital converter may be selected from a flash analog-to-digital converter (FADC) or a field-programmable gate array (FPGA) or a VME digitizer or a oscilloscope or a TDC readout board (TRB). Further, the evaluation device 150 may be connected to a monitor 152 and a keyboard 154 which may, preferably, be located outside the detector 110. Alternatively or in addition, a processing device (not depicted here) may also be connected, in a wire-bound or a wireless fashion, to the evaluation device 150, wherein the processing device may be designed for controlling the evaluation device 150, such as in a master-slave relationship. However, further kinds of processing devices may also be feasible.

As further illustrated in FIG. 1A, the detector segment 130 absorbs only a small portion of energy of the incident ion beam 114, from which portion radiation is generated upon passing of a single particle 112 as comprised by the bunch 116 of ions 118 through the detector segment 130. However, the ion beam 114 passes the detector segment 130 without being absorbed by the scintillating fibers 132 as comprised by the fiber layer 136 being located perpendicularly with respect to the direction 122 of the incident ion beam 114. In the preferred embodiment of the detector 110 as illustrated in FIG. 1A, the ion beam 114, which may be denoted as an outgoing beam 156 after having passed the detector segment 130 without being absorbed, passes an exit window 158 which may be provided within a portion of the housing 126, wherein the exit window 158 may, similar to the entrance window 128, especially be designed for exhibiting a high transparency for those kinds of ions 118 which are comprised for the ion beam 114, such as $^{12}C$ ions, and a low transparency for all other kind of radiation.

As further illustrated in FIG. 1A, after having passed the exit window 158, the ion beam 114 is now ready for a treatment of a tissue 160 of a patient. In a further event in which the ion beam 114 may impinge on the tissue 160 of the patient, the incident ion beam 114 may generate there at least prompt-gamma radiation 162 and neutrons, beta emitters, secondary charged particles (not depicted here). Herein, a further detector 164 which may be connected to an apparatus 166 for a verification of a particle range and a dose delivery in the tissue 160 of the patient may be placed at a distance from the tissue 160, wherein the further detector 164 may also be linked to the evaluation device 150. Herein, the evaluation device 150 may be designated to function as a combined evaluation device which may further be designed for determining particle energy and time-of-flight measurements by using measurements of the prompt-gamma radiation 162 received by the further detector 164 and measurements of the single particles 112 received by the detector segment 130. However, other arrangements of the apparatus 166, specifically for measuring prompt-gamma radiation 162, may also be feasible.

FIG. 2A illustrates a further preferred embodiment of the detector 110 for tracking the arrival time of the single particles 112 in the ion beam 114 in a top view and two preferred embodiments of a portion of the detector 110 are shown in side views (FIGS. 2B and 2C). Herein, the detector 110 comprises, as further illustrated in each of FIGS. 2A, 2B and 2C, the two detector elements 140, 140', wherein both the first detector element 140 and the second detector element 140' are designed for generating a measurable detector signal from the scintillation. In this further embodiment, the two detector elements 140, 140' are arranged in a fashion that the connection 144 to the scintillating fibers 132 as provided in the fiber layer 136 is provided in an alternating manner. As particularly illustrated in FIG. 2B, this kind of connection 144 may comprise the first readout bundle 146 of the first, the third, the fifth, etc. scintillating fiber 132 to the first detector element 140 and, concurrently, the second readout bundle 146' of the second, the fourth, the sixth, etc. scintillating fiber 132 to the second detector element 140'. However, other kinds of connections 144 may also be feasible, such as scintillating fibers arranged in a consecutive manner. As particularly illustrated in FIG. 2C, a further kind of connection 144 may comprise the two individual readout bundles 146, 146' which connect a first end of each of the scintillating fibers 132 to first detector element 140 and, concurrently, a second end of each of the scintillating fibers 132 to the second detector element 140'.

Further, the detector signals as provided by the two individual detector elements 140, 140', respectively, are further delivered by the corresponding leads 148, 148' to the evaluation device 150, wherein the evaluation device 150 is designated here for determining the information about the single particles 112 from the detector signals which are provided by both detector elements 140, 140'. For this purpose, a wire-based connection or, alternatively or in addition, a wireless connection, such as by using optical or radio frequency transmission, between each of the detector elements 140, 140' and the evaluation device 150 may be provided. Thus, the evaluation device 150 is designed for determining the tracking information about the single particles 112 based on the detector signals which are provided by both detector elements 140, 140' to the evaluation device 150.

Figure 2:
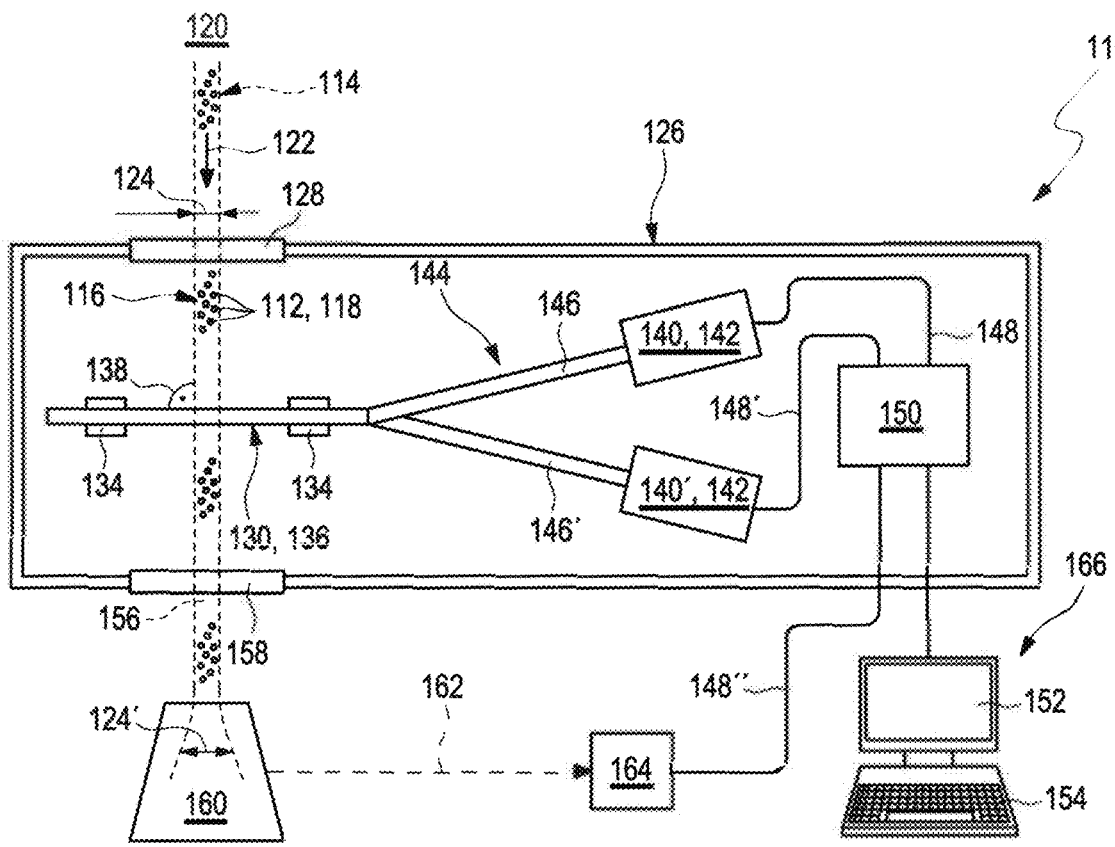
FIGS. 2A, 2B and 2C illustrate a further preferred embodiment of the detector for tracking the arrival time of the single particles in the ion beam comprising two individual detector elements in a top view (FIG. 2A) and two preferred embodiments of a portion of the detector in a side view (FIGS. 2B and 2C)
Figure 2:
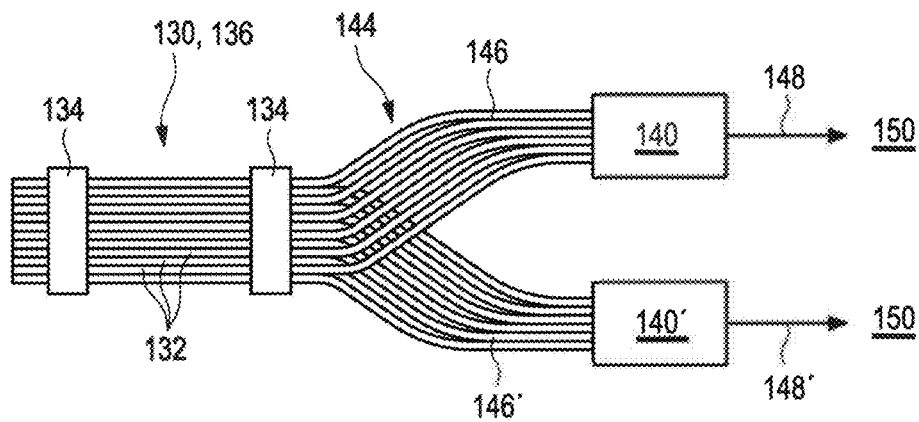
Figure 2:
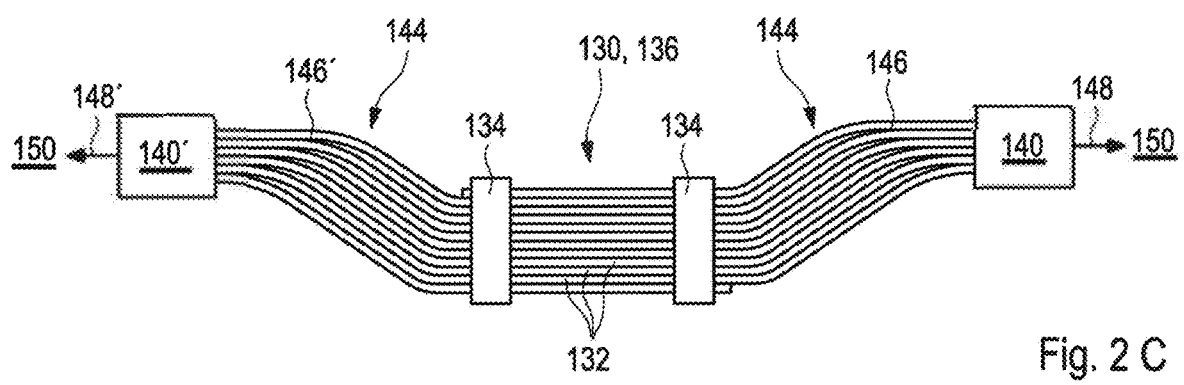

For a detailed description of further features as illustrated in FIG. 2, reference may be made to the description of FIG. 1 above.

Figure 3:
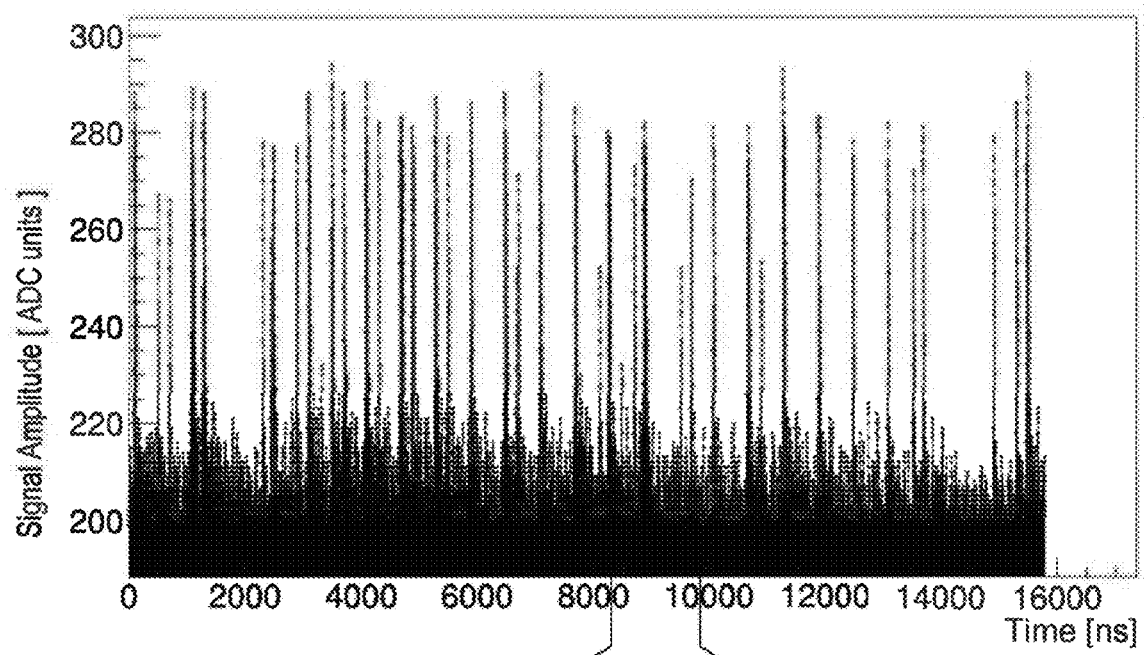
FIGS. 3A and 3B illustrate measured time-resolved micro-structures of an ion beam at a microsecond scale (0-16.000 ns in FIG. 3A) and at a nanosecond scale (8200-9800 ns in FIG. 3B) as recorded by using the detector for tracking the arrival time of the single particles in the ion beam according to FIG. 1.
Figure 3:
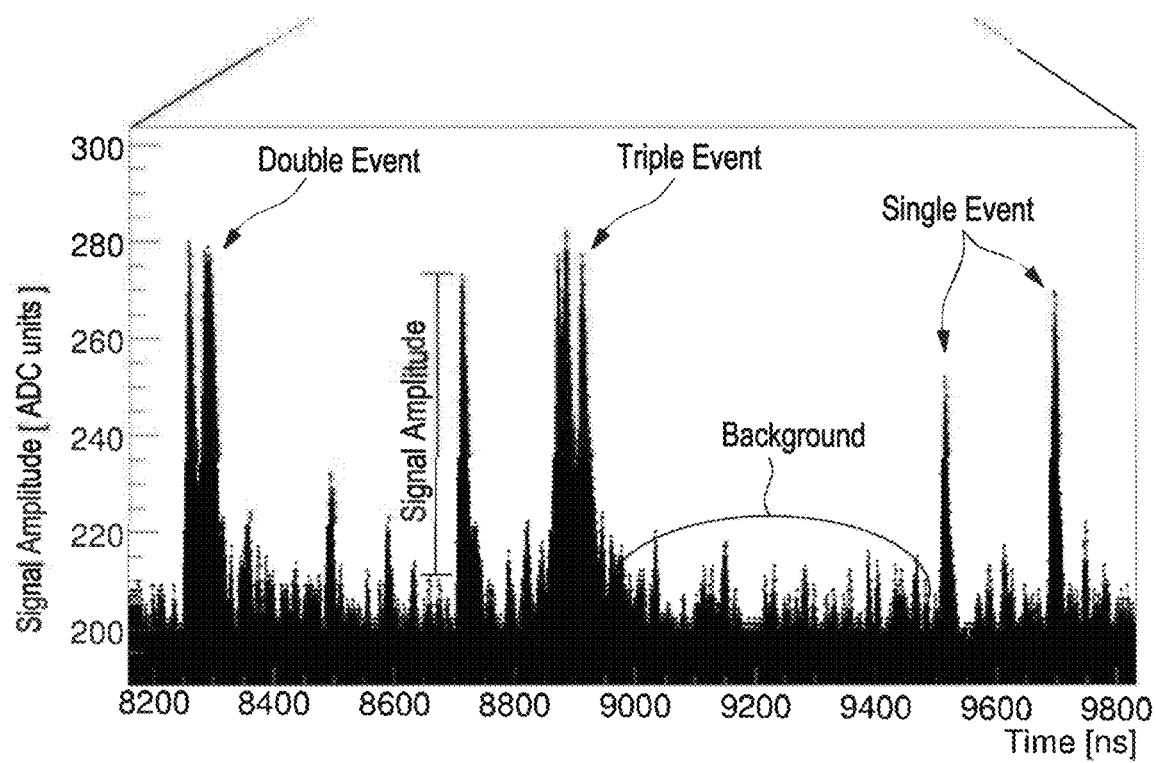

FIG. 3A illustrates a time-resolved micro-structure of the ion beam 114 at a microsecond scale as signal amplitude in ADC units (the units in which the digital number output of the ADC or raw values are measured) over a time scale of 0 ns to 16.000 ns which has been recorded by using the detector 110 according to this disclosure, specifically by the detector 110 as described above in connection with FIG. 1, for tracking the $^{12}C$ ions in a beam having an initial energy of 176 MeV/u and an intensity of $3 \times 10^7$ ions/s. Herein, the time-resolved micro-structure of the ion beam 114 reveals a multitude of consecutive events which are characterized by significant signal amplitudes, such as of 260 to 300 ADC units, compared to a background noise characterized by insignificant signal amplitudes, such as of 220 ADC units or below. In particular, FIG. 3A confirms the above-indicated observation that, due to different acceleration processes in a synchrotron compared to a cyclotron, the ion beam 114 which is generated in the synchrotron 120 exhibits an irregular microscopic time structure. As indicated above, this irregular microscopic time structure as illustrated in FIG. 3A, is the reason for the inexistent correlation between the radio frequency as used in the synchrotron 120 and the temporal microstructure of the generated ion beam 114, thus making it impossible to use such a correlation for indirect determination of time-of-flight (TOF) information.

FIG. 3B shows an enlarged section of the illustration of FIG. 3A over a time scale of 8200-9800 ns. Specifically, FIG. 3B demonstrates that the detector 110 may even be capable of providing a time resolution not only for single events but also for multiple events, such as a double event or a triple event, within a bunch. Herein, the multiple events are expected to occur in an occasion in which more than one single particle 112, such as two, three or more single particles 112, enters the detector segment 130 within the same bunch.

Figure 5:
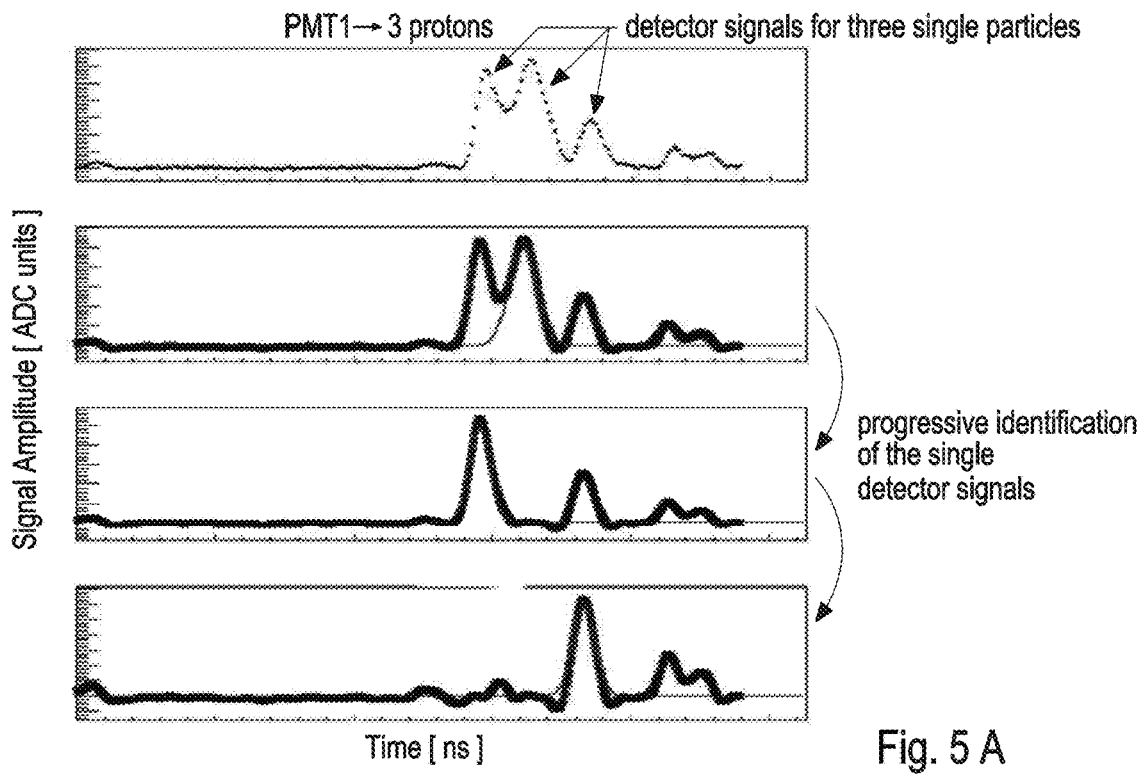
FIGS. 5A and 5B illustrate experimental results which demonstrate a resolution of single protons at a beam intensity of $8 \times 10^7$ $^1$p/s as recorded by using the detector for tracking the arrival time of the single particles in the ion beam according to FIG. 2 and obtained with a first photo multiplier tube (PMT1.
Figure 5:
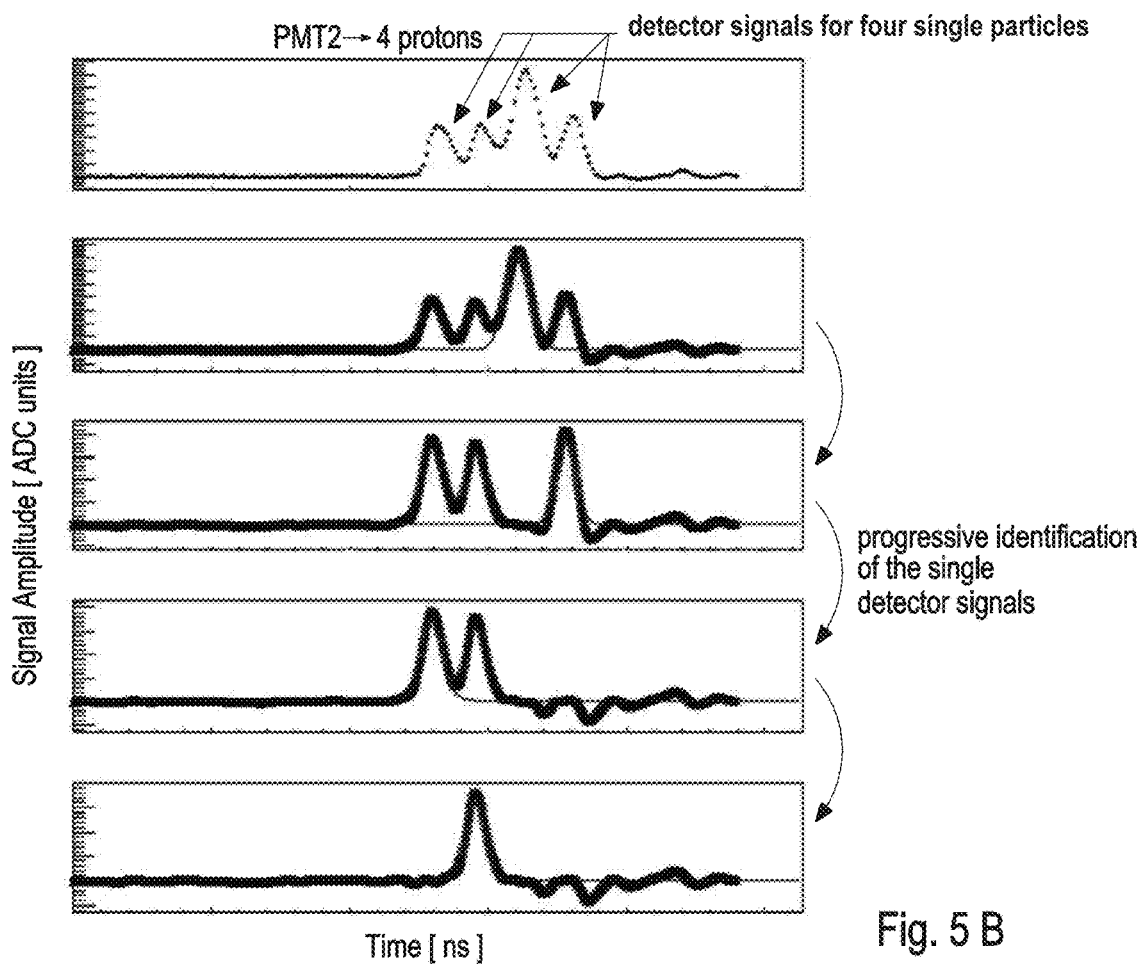

As presented in Table 1 below, preliminary experiments have shown that the design of the detector 110 according to this disclosure is scalable to cover a whole irradiated area also at higher clinical intensities. The calculations are based on beam properties of the Heidelberg Ion-beam Therapy Center (HIT, Heidelberg, Germany) synchrotron. Similar properties are shared by other clinical synchrotron-based facilities. For proton beams, a highest available clinical intensity can amount to $2 \times 10^9$ p/s, and the minimum lateral spread 124 of the bunches 116 is 29.3 mm with an average time separation between the bunches of 150 ns. This means that, in average, each bunch may comprise 300 single particles, wherein these 300 single particles may be distributed in space over the lateral spread 124 being 29.3 mm wide covering 59 individual scintillating fibers, when considering a diameter of 500 µm for each scintillating fiber. Herein, the scintillating fibers can be connected in an alternated geometry with an alternation period of at least 59 scintillating fibers to at least 59 independent detector elements 140, 140', . . . . This means that, in average, each detector element 140, 140', . . . records the detector signals from a maximum of 5 protons, which can be easily separated as, for example, demonstrated in FIG. 5 below.

For carbon beams, the highest available clinical intensity can amount to $5 \times 10^7$ ions/s and the minimum lateral spread 124 of the bunches may be 10.5 mm with an average time separation between the bunches 116 of 150 ns. This means that, in average, each bunch 116 may comprise 7.5 single particles which may be distributed in space over the 10.5 mm wide lateral spread 124 covering 21 individual scintillating fibers, when considering a diameter of 500 µm for each scintillating fiber. Herein, the scintillating fibers can be connected in an alternated geometry with an alternation period of at least 21 scintillating fibers to at least 21 independent detector elements 140, 140', . . . . This means that, in average, each detector element 140, 140', . . . records the detector signals from a maximum of 0.35 carbon ions, which can be easily separated as demonstrated in FIG. 5.

Further, in order to cover a scanning area of 20×20 cm² the detector segment 130 may, preferably, extend over 20 cm in both directions being perpendicular to the beam direction 122. In one of these directions, a total number of 400 scintillating fibers can, preferably, be used when considering a diameter of 500 µm for each scintillating fiber whereas up to 20,000 scintillating fibers can, preferably, be used when considering a diameter of 10 µm for each scintillating fiber. In the other of these directions, each of the single scintillating fibers can, preferably, be selected to have a length which may be designed to cover the extension of the detector segment 130 of 20 cm. As a result, the detector 110 may be scalable to cover a whole irradiated area also at higher clinical intensities.

TABLE 1

| Property | Proton beams | Carbon beams |
|---|---|---|
| Maximum clinical intensity | $2 \times 10^9$ p/s | $5 \times 10^7$ ions/s |
| Minimum spot size (F1, ±3σ) | 29.3 mm | 10.5 mm |
| Number of scintillating fibers inside the lateral spread of the spot | 59 scintillating fibers (diameter of 500 µm) | 21 scintillating fibers (diameter of 500 µm) |
| Average bunch separation | 150 ns | 150 ns |
| Average events per scintillating fiber per bunch | <5 protons | <0.35 ions |

Figure 4:
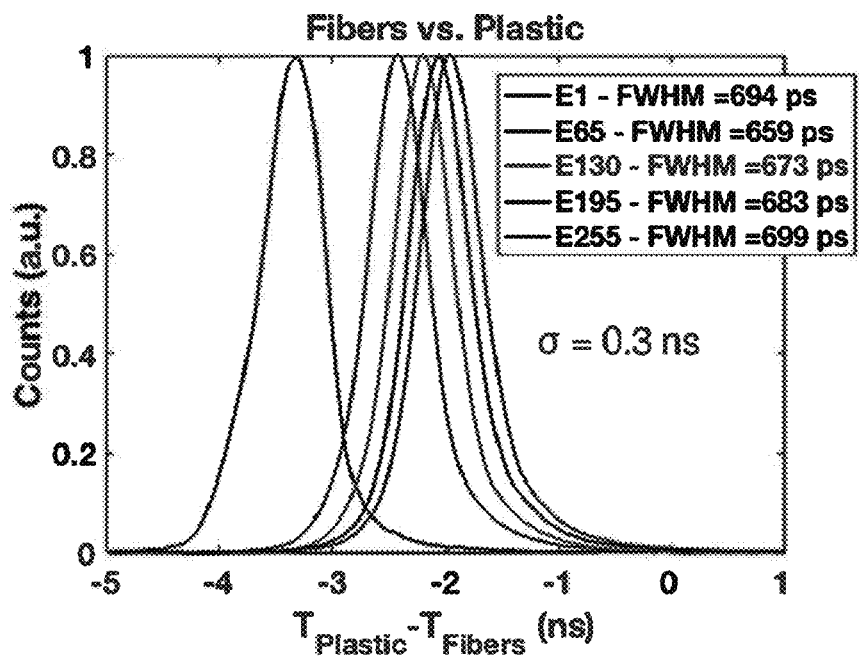
FIGS. 4A and 4B illustrate measured time of flight resolutions as further recorded by using the detector for tracking the arrival time of the single particles in the ion beam according to FIG. 1 in correlation to a charged particle detector as known from prior art (FIG. 4A) and the time of flight resolution recorded by using the detector for tracking the arrival time of the single particles in the ion beam according to FIG. 1 in correlation to a gamma detector as known from prior art (FIG. 4B)
Figure 4:
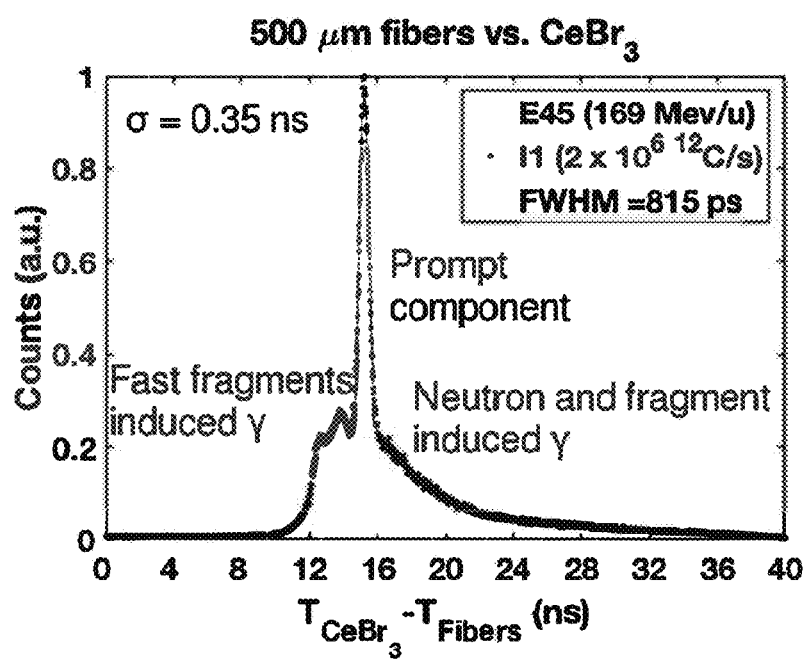

FIG. 4A illustrates measured time of flight resolutions in nanoseconds (ns) as counts in arbitrary units (a.u.) which has been recorded by measuring the time difference of the detector signals as obtained by using the detector 110 according to this disclosure, specifically by the detector 110 as described above in connection with FIG. 1, compared to detector signals as obtained by using a charge particle detector as known from prior art, specifically a plastic scintillator detector having a thickness of 4 mm coupled to a photomultiplier tube placed between the exit window 158 and the tissue 160 (not illustrated here). The measurements as presented in FIG. 4A can be considered as an upper limit for an intrinsic time resolution of the detector 110 for the tracking of the arrival time of single particles 112. The measured time resolution is <1 ns, specifically a sigma width was measured to be 0.3 ns.

Moreover, FIG. 4B displays measured time of flight resolutions in nanoseconds (ns) as counts in arbitrary units (a.u.) which has been recorded by measuring a time difference of the detector signals obtained by using the detector 110 according to this disclosure, specifically by the detector 110 as described above in connection with FIG. 1, compared to detector signals as obtained by using a further detector 164 for gamma radiation as known from prior art, specifically a cerium bromide $CeBr_3$ scintillator crystal coupled to a photomultiplier tube (not illustrated here). The measurements as presented in FIG. 4B represent the upper limit for the time resolution of the detector 110 for the time of flight between the single particles 112 and the prompt gamma radiation 162. The measured time resolution is <1 ns, specifically the sigma width was measured to be 0.35 ns.

FIGS. 5A and 5B illustrate experimental results in nanoseconds (ns) as signal amplitude in ADC counts which demonstrate measured detector signals of single protons at a beam intensity of $8 \times 10^7$ p/s as recorded with a first photo multiplier tube (PMT1; FIG. 5A) and a second photo multiplier tube (PMT2; FIG. 5B), respectively, during a delivery of a single bunch 116. Herein, FIGS. 5A and 5B have been obtained by applying a common time scale in the evaluation device 150 to the detectors signals as measured by the detector elements 140, 140' during the delivery of a single bunch 116 by the synchrotron 120. In this exemplary embodiment, the bunch 116 comprises seven single particles 112 which are spatially distributed along the lateral spread 124 and temporally distributed along the bunch 116 width of few nanoseconds. Due to the lateral spread 124, when the single particles 112 reach the fiber layer 136, some of them interact with the scintillating material 132 connected to the first detector element 140 and the others interact with the scintillating material 132 connected with the second detector element 140' as the single fibers in the fiber layer 136 being independent among each other, wherein the detector elements 140, 140' are also independent among each other.

Specifically, FIGS. 5A and 5B illustrate a case in which the detector signals of three single particles 112 are recorded by the first detector element 140 (PMT1, FIG. 5A) and the detector signals of four single particles 112 are recorded by the second detector element 140' (PMT2, FIG. 5B). Therefore, the detector signals as generated by the single protons are stochastically distributed among the detector elements 140, 140', which avoids that two simultaneous detector signals may overlap. Thus, the overlap of multiple detector signals is avoided, such that it is, therefore, possible to identify and separate the single detector signals, as illustrated in FIG. 5A for three detector signals and in FIG. 5B for four detector signals. In particular, at every iteration step the detector signal having the highest signal amplitude can be identified and be removed from the data until no detector signal may be left.

Figure 6:
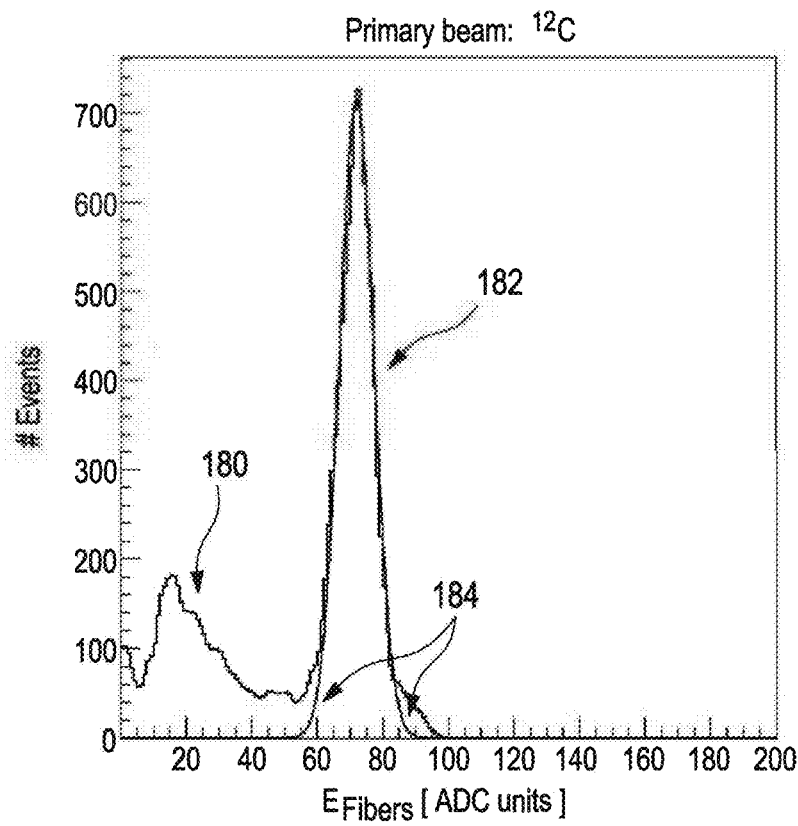
FIGS. 6A and 6B illustrate separating a proton $^1$p contamination within a primary ion beam comprising carbon ions $^{12}$C by observing an energy deposition according to a particular embodiment of this disclosure (FIG. 6A) compared to a primary beam comprising protons $^1$p (FIG. 6B)
Figure 6:
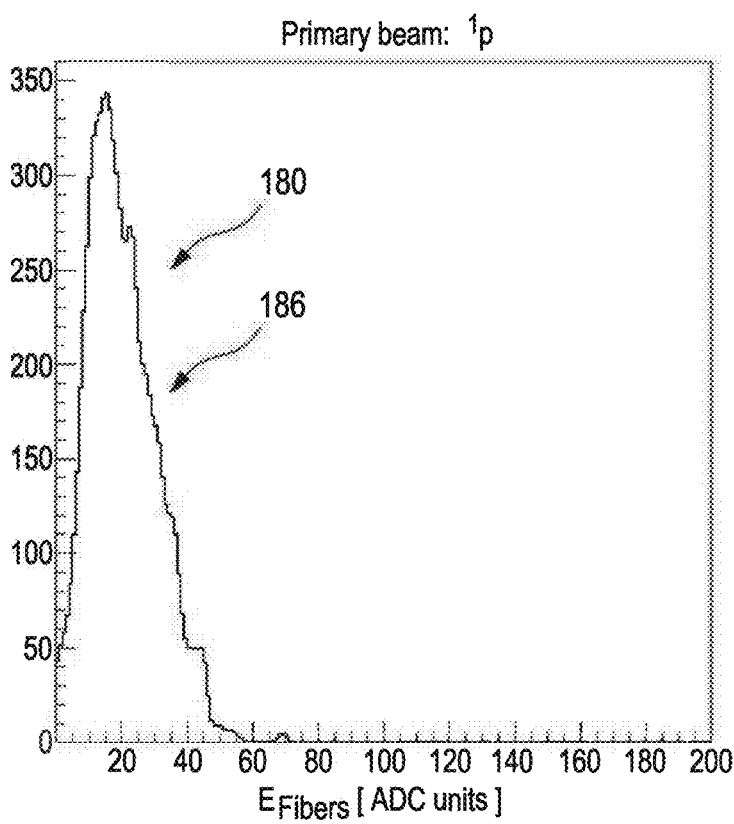

FIG. 6A schematically illustrates a method for determining a type of the single particles 112 in the ion beam 114 in accordance with a further embodiment. Accordingly, separating a proton $^1$p component 180 as a contamination within the ion beam 114 comprising a carbon ion $^{12}$C component 182 may be achieved by observing a course of an energy deposition $E_{Fibers}$ on the scintillating fibers 132, which can be considered as an envelope curve 184. As shown in FIG. 6A, the proton $^1$p component 180, which, predominantly, contributes below 60 ADC units, can be easily separated from the carbon ion component 182, which, predominantly, contributes above 60 ADC units. This result is confirmed by FIG. 6B which shows a curve 186 exhibiting an energy deposition $E_{Fibers}$ on the scintillating fibers 132 of a primary ion beam which only comprises protons $^1$p, predominantly, contributes only below 60 ADC units.

Figure 7:
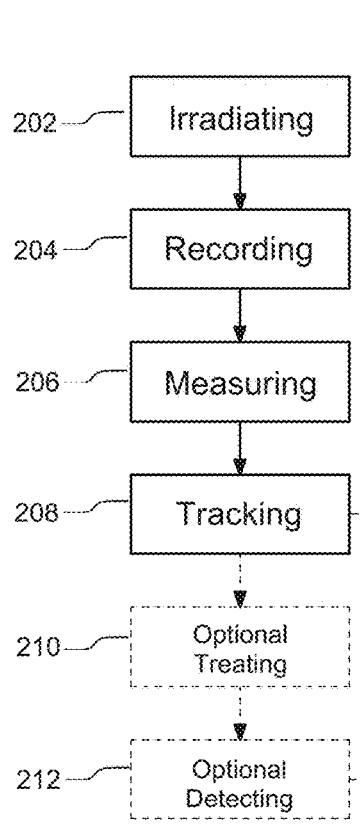
FIG. 7 illustrates a preferred embodiment of a method for tracking the arrival time of the single particles in the ion beam in accordance with this disclosure.

FIG. 7 illustrates a preferred embodiment of a method 200 for tracking the single particles 112 in the incident ion beam 114 in accordance with this disclosure.

According to an irradiating step 202, the incident ion beam 114 is provided by using by the synchrotron 120, wherein the ion beam 114 as provided comprises a plurality of single particles 112 some of which are travelling together in a bunch 116 of ions 118.

In a recording step 204, the fiber layer 136 is arranged, before, after, or concurrently with the irradiating step 202, in a manner that the incident ion beam 114 impinges on the fiber layer 136 perpendicularly with respect to the direction 122 of the incident ion beam 114. For this purpose, the fiber layer 136 as provided comprises the plurality of the scintillating fibers 132, wherein each of the scintillating fibers 132 comprises the scintillating material 130. As a result, the scintillating material 132 generates the radiation upon an event which is triggered by the passing of the single particle 112 through the scintillating material 132.

In a measuring step 206, the detector signal is generated in the at least one detector element 140, 140' from the radiation as generated in the recording step 204. For the purpose of operating the detector 110 with higher clinical intensities, the detector elements 140, 140' may, as illustrated in FIG. 2, alternatingly connected to the scintillating fibers 132 within the fiber layer 136 as described above in more detail.

In a tracking step 208, information about the single particles 112 is determined from the detector signals that are provided by the detector elements 140, 140' during the measuring step 206 by using the evaluation device 150.

In a further optional treating step 210, the incident ion beam 114 which passes unabsorbed through the detector segment 130 is delivered in a direction in order to impinge on the tumorous tissue 160 of the patient.

In a further optional detecting step 212, prompt-gamma radiation which is generated by the ion beam 114 which impinges on the tissue 160 of the patient is measured by the further detector 162 which is designated for such a purpose.

By adding a further optional determining step 214, the type of the single particles 112 in the ion beam 114 can be determined by observing a course of an energy deposition on the fiber layer 134 as comprised by the detector 110.

For further details with respect to the method 200 for tracking the single particles 112 in the incident ion beam 114, reference can be made to the description of the detector 110 as provided above.

Figure 8:
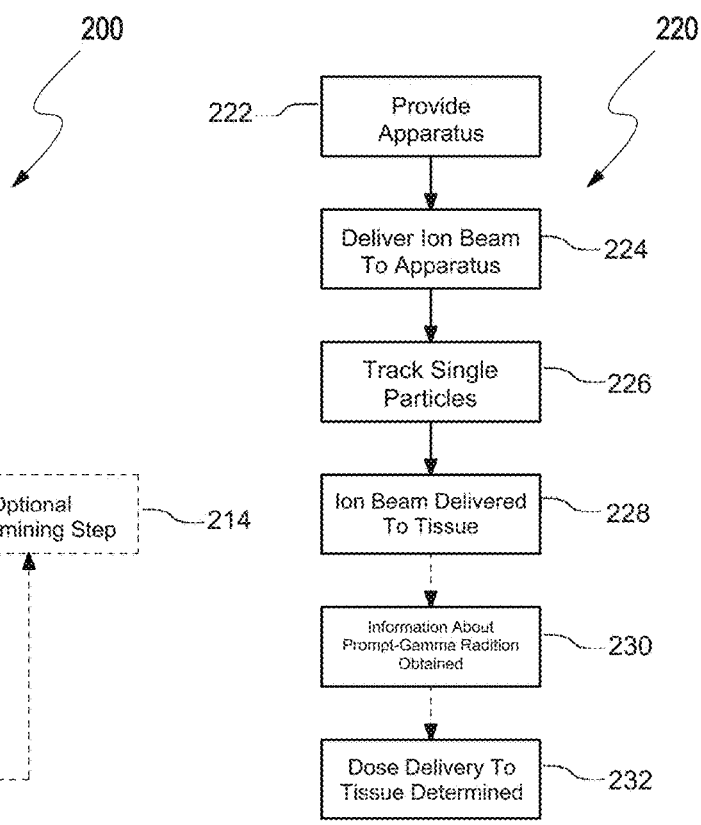
FIG. 8 illustrates a preferred embodiment of a method for verification of the particle range and the dose delivery in a tissue of a patient in accordance with this disclosure.

FIG. 8 illustrates a preferred embodiment of a method 220 for verification of a particle range and a dose delivery in the tissue 160 of the patient in accordance with this disclosure.

According to a providing step 222, the apparatus 166 for verification of the particle range and the dose delivery in the tissue 160 of the patient is provided.

In a delivering step 224, the incident ion beam 114 as being provided by the synchrotron 120 is delivered to the apparatus 166, wherein the ion beam 114 comprises the single particles 112 in the bunch 116 of ions 118.

In a tracking step 226, the single particles 112 in the ion beam 114 are tracked by applying the detector 110 in accordance with the method 200 for tracking the single particles 112 in the incident ion beam 114 as described above in more detail.

In a further delivering step 228, the ion beam 114 which is not absorbed by the fiber layer 136 as comprised by the detector 110 is delivered to the tissue 160 of the patient. As a result, the prompt-gamma radiation 162 is generated by the ion beam 114 in the tissue 160 of the patient.

In a further determining step 230, information about the prompt-gamma radiation 163 as being generated by the tissue 160 of the patient is obtained, specifically by using the further detector 164.

In a further verifying step 232, the particle range and the dose delivery to the tissue 160 of the patient is determined based on the information about the prompt-gamma radiation 162, specifically received by the evaluation device 150 by a further wire-bound or wireless lead 148" from the further detector 164.

For further details with respect to the method 220 for verification of the particle range and dose delivery in the tissue 160 of the patient, reference can be made to the description of the detector 110 as provided above.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMBERS 110 detector
112 single particle
114 incoming ion beam
116 bunch
118 ion (hadron)
120 synchrotron
122 direction
124 lateral spread
126 housing
128 entrance window
130 detector segment
132 scintillating material
134 mounting
136 fiber layer
138 perpendicular arrangement
140,140' detector element
142 photomultiplier tube (PMT)
144 connection
146,146' readout bundle
148,148',148" lead
150 evaluation device 152 monitor
154 keyboard
156 outgoing ion beam
158 exit window
160 tissue
162 prompt-gamma radiation
164 further detector
166 apparatus
180 proton component
182 carbon ion component
184 envelope curve
186 curve
200 method for tracking an arrival time of single particles in an ion beam
202 irradiating step
204 recording step
206 measuring step
208 tracking step
210 treating step
212 detecting step
214 determining step
220 method for verification of a particle range and a dose delivery in a tissue of a patient
222 providing step
224 delivering step
226 tracking step
228 further delivering step
230 determining step
232 verifying step

What is claimed is:

1. A detector for tracking an arrival time of single particles in an ion beam in which single particles are provided as a bunch of ions by a synchrotron, the detector comprising:
a scintillating material configured for generating radiation upon passing therethrough of a single particle, the scintillating material comprising a fiber layer formed from scintillating fibers, wherein the fiber layer is arranged perpendicular to a direction of the incident ion beam;
a detector element configured for generating a detector signal from the radiation; and
a processor configured for determining the type of the single particles from the detector signals provided by the detector element as a function of a course of an energy deposition on a fiber layer that is connected to an individual detector element.

2. The detector of claim 1, wherein the detector element comprises at least two detector elements.

3. The detector of claim 2, wherein the at least two detector elements are alternatingly connected to the scintillating fibers within the fiber layer.

4. The detector of claim 1, wherein the fiber layer comprises 10 to 20,000 scintillating fibers.

5. The detector of claim 1, wherein each of the scintillating fibers has a cross-section of 10 μm to 10 mm.

6. The detector of claim 1, wherein the detector element is selected from at least one of a photomultiplier tube, a silicon photomultiplier, a charge-coupled device, a complementary metal-oxide-semiconductor, a quanta image sensor chip.

7. The detector of claim 1, wherein the processor is configured for determining time information about the single particles from the detector signals provided by the detector element.

8. The detector of claim 1, wherein the processor comprises a data acquisition system, wherein components of the data acquisition system are selected from at least one of: FADC, FPGA, VME digitizer, TRB, oscilloscope.

9. An apparatus for verification of a particle range and a dose delivery in a tissue of a patient, the apparatus comprising:
the detector of claim 1;
a further detector configured for determining prompt-gamma radiation generated by interaction of the ion beam with the tissue of the patient; and
a further processor configured for verification of the particle range and the dose delivery in the tissue of the patient.

10. The apparatus of claim 9 wherein the detector is placed into a path of the ion beam traveling from a synchrotron to the tissue of the patient.

11. The apparatus of claim 9 wherein the further detector is arranged perpendicular to the direction of the incident ion beam.

12. The apparatus of claim 9, wherein the further evaluation device and the evaluation device of the detector are integrated into a combined evaluation device for time-of-flight measurements between the evaluation device and the further evaluation device.

13. A method for verification of a particle range and a dose delivery in a tissue of a patient, the method comprising:
providing an apparatus of claim 9;
delivering an incident ion beam from a synchrotron to the apparatus, the ion beam comprising single particles in a bunch of ions;
tracking an arrival time of the single particles in the ion beam using the detector;
delivering a portion of energy of the ion beam which is not absorbed by the scintillating material to the tissue of the patient, wherein the portion of energy of the ion beam generates prompt-gamma radiation;
determining information about the prompt-gamma radiation being generated by an interaction of the beam with the tissue of the patient; and
verifying the particle range and the dose delivery to the tissue of the patient based on the information about the prompt-gamma radiation.

14. A method for tracking an arrival time of single particles in an ion beam, the method comprising:
delivering an incident ion beam from a synchrotron to a fiber layer, the ion beam comprising single particles in a bunch of ions and the fiber layer formed from scintillating fibers, each of the scintillating fibers comprising a scintillating material;
impinging the incident ion beam on the fiber layer in a direction perpendicular to the direction of the incident beam;
passing a particle from the bunch of ions through the scintillating material and thereby generating radiation;
using a detector element to generate a detector signal from the radiation;
using a processor to determine information about the single particles from the detector signals provided by the detector element; and
delivering a portion of energy of the incident ion beam, which passes unabsorbed through the scintillating material, to impinge on a tissue of a patient.

15. The method of claim 14, further comprising measuring prompt-gamma radiation that is generated by the interaction of the ion beam with the tissue.

16. The method of claim 14, wherein the detector signal from the radiation is generated in at least two detector elements, wherein the at least two detector elements are alternatingly connected to the scintillating fibers within the fiber layer.

17. A method for determining a type of single particles in an ion beam, the method comprising:

delivering an incident ion beam from a synchrotron to a fiber layer, the ion beam comprising single particles in a bunch of ions and the fiber layer formed from scintillating fibers, each of the scintillating fibers comprising a scintillating material;

impinging the incident ion beam on the fiber layer in a direction perpendicular to the direction of the incident beam;

passing a particle from the bunch of ions through the scintillating material and thereby generating radiation;

using a detector element to generate a detector signal from the radiation;

using a processor to determine information about the single particles from the detector signals provided by the detector element; and determining the type of the single particles in the ion beam by observing a course of an energy deposition on a fiber layer that is connected to an individual detector element.

18. The method of claim 17, wherein the type of the single particles in the ion beam is determined by separating a contribution of at least one ion component from an envelope curve provided by the course of the energy deposition on the fiber layer.

19. The method of claim 17, wherein a contamination of protons within the ion beam of helium, carbon or oxygen ions is determined.

* * * * *